US009241920B2

(12) United States Patent
Aifantis et al.

(10) Patent No.: US 9,241,920 B2
(45) Date of Patent: Jan. 26, 2016

(54) INHIBITION OF C-MYC UBIQUITINATION TO PREVENT CANCER INITIATION AND PROGRESSION

(71) Applicants: Iannis Aifantis, Brooklyn, NY (US); Linsey Reavie, Binningen (CH); Shannon Buckley, New York, NY (US)

(72) Inventors: Iannis Aifantis, Brooklyn, NY (US); Linsey Reavie, Binningen (CH); Shannon Buckley, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/354,822

(22) PCT Filed: Oct. 29, 2012

(86) PCT No.: PCT/US2012/062388
§ 371 (c)(1),
(2) Date: Apr. 28, 2014

(87) PCT Pub. No.: WO2013/063560
PCT Pub. Date: May 2, 2013

(65) Prior Publication Data
US 2014/0288178 A1 Sep. 25, 2014

Related U.S. Application Data

(60) Provisional application No. 61/552,315, filed on Oct. 27, 2011.

(51) Int. Cl.
| A61K 31/506 | (2006.01) |
| A61K 31/196 | (2006.01) |
| A61K 45/06 | (2006.01) |
| A61K 38/17 | (2006.01) |
| A61N 5/10 | (2006.01) |

(52) U.S. Cl.
CPC ............ *A61K 31/196* (2013.01); *A61K 31/506* (2013.01); *A61K 38/1709* (2013.01); *A61K 45/06* (2013.01); *A61N 5/10* (2013.01)

(58) Field of Classification Search
None
See application file for complete search history.

(56) References Cited

U.S. PATENT DOCUMENTS

2004/0192652 A1  9/2004  Giles et al.
2010/0004232 A1  1/2010  Berdini et al.

FOREIGN PATENT DOCUMENTS

WO    2006104672 A1   10/2006

OTHER PUBLICATIONS

Jiang et al., "Chronic Myeloid Leukemia Stem Cells Possess Multiple Unique Features of Resistance to BCR-ABL Targeted Therapies," Leukemia 21:926-935 (2007).
Orlicky et al., "An Allosteric Inhibitor of Substrate Recognition by the SCF (Cdc4) Ubiquitin Ligase," Nat Biotechnol 28(7):733-738 (2010).
Aghajanyy et al., "Chemical Genetics of TOR Identifies an SCF Family E3 Ubiquitin Ligase Inhibitor," Nat Biotechnol 28(7):738-742 (2010).
Prochownik et al., "Therapeutic Targeting of Myc," Genes & Cancer 1(6):650-659 (2010).

(Continued)

*Primary Examiner* — Anna Pagonakis
(74) *Attorney, Agent, or Firm* — LeClairRyan, a Professional Corporation

(57) ABSTRACT

The present invention is directed to methods of inhibiting cancer cell proliferation, differentiation and/or survival. These methods involve the administration of Fbw7 E3 ligase inhibitors to inhibit c-Myc ubiquitination in cancerous cell populations, such as leukemic initiating cell populations, that are responsible for disease initiation and progression.

10 Claims, 24 Drawing Sheets

(56) References Cited

OTHER PUBLICATIONS

Savino et al., "The Action Mechanism of the Myc Inhibitor Termed Omomyc May Give Clues on How to Target Myc for Cancer Therapy," Plos One 6(7):1-16 (2011).
Hermeking, Heiko, "The MYC Oncogene as a Cancer Drug Target," Current Cancer Drug Targets 3:163-175 (2003).
Sun, Yi, "Targeting E3 Ubiquitin Ligases for Cancer Therapy," Cancer Biology & Therapy 2(6):623-629 (2003).
Meijer et al., "Pharmacological Inhibitors of Glycogen Synthase Kinase 3," Trends in Pharmacological Sciences 25 (9):471-480 (2004).
Bagnasco et al., "Inhibition of a Protein-protein Interaction Between INI1 and c-Myc by Small Peptidomimetic Molecules Inspired by Helix-1 of c-Myc: Identification of a New Target of Potential Antineoplastic Interest," The FASEB Journal 21:1256-1263 (2007).
Aghajan et al., "Chemical Genetics Screen for Enhancers of Rapamycin Identifies a Specific Inhibitor of an SCF Family E3 Ubiquitin Ligase," Nat Biotechnol 28(7):738-744 (2010).
Nakayama et al., "Ubiquitin Ligases: Cell-cycle Control and Cancer." Nature Reviews 6:369-381 (2006).
PCT International Search Report and Written Opinion corresponding to PCT/US2012/062388, filed Oct. 29, 2012 (mailed Mar. 27, 2013).

SEQUENCE LISTING

```
<160> NUMBER OF SEQ ID NOS: 33

<210> SEQ ID NO 1
<211> LENGTH: 22
<212> TYPE: RNA
<213> ORGANISM: Artificial
<220> FEATURE:
<223> OTHER INFORMATION: has-miR-27a

<400> SEQUENCE: 1
agggcuuagc ugcuugugag ca                                              22

<210> SEQ ID NO 2
<211> LENGTH: 22
<212> TYPE: RNA
<213> ORGANISM: Artificial
<220> FEATURE:
<223> OTHER INFORMATION: has-miR-223

<400> SEQUENCE: 2
cguguauuug acaagcugag uu                                              22

<210> SEQ ID NO 3
<211> LENGTH: 18
<212> TYPE: PRT
<213> ORGANISM: Artificial
<220> FEATURE:
<223> OTHER INFORMATION: TRIP-BR decoy peptide

<400> SEQUENCE: 3

Ala Thr Gly Cys Leu Leu Asp Asp Gly Leu Glu Gly Leu Phe Glu Asp
1               5                   10                  15

Ile Asp

<210> SEQ ID NO 4
<211> LENGTH: 18
<212> TYPE: PRT
<213> ORGANISM: Artificial
<220> FEATURE:
<223> OTHER INFORMATION: TRIP-BR decoy peptide
```

-continued

```
<400> SEQUENCE: 4

Thr Gly Phe Leu Thr Asp Leu Thr Leu Asp Asp Ile Leu Phe Ala Asp
1               5                   10                  15

Ile Asp

<210> SEQ ID NO 5
<211> LENGTH: 78
<212> TYPE: DNA
<213> ORGANISM: Artificial
<220> FEATURE:
<223> OTHER INFORMATION: KH1C12 aptamer

<400> SEQUENCE: 5
atccagagtg acgcagcatg ccctagttac tactactctt tttagcaaac gccctcgctt      60
tggacacggt ggcttagt                                                    78

<210> SEQ ID NO 6
<211> LENGTH: 21
<212> TYPE: DNA
<213> ORGANISM: Artificial
<220> FEATURE:
<223> OTHER INFORMATION: FBW7 primer

<400> SEQUENCE: 6
ggcttagcat atcagctatg g                                                21

<210> SEQ ID NO 7
<211> LENGTH: 22
<212> TYPE: DNA
<213> ORGANISM: Artificial
<220> FEATURE:
<223> OTHER INFORMATION: FBW7 primer

<400> SEQUENCE: 7
atagtaatcc tcctgccttg gc                                               22

<210> SEQ ID NO 8
<211> LENGTH: 23
<212> TYPE: DNA
<213> ORGANISM: Artificial
<220> FEATURE:
<223> OTHER INFORMATION: FBW7 primer

<400> SEQUENCE: 8
attgatacaa actggagacg agg                                              23

<210> SEQ ID NO 9
<211> LENGTH: 21
<212> TYPE: DNA
<213> ORGANISM: Artificial
<220> FEATURE:
<223> OTHER INFORMATION: MxCre primer

<400> SEQUENCE: 9
gcctacaata tggatttccc a                                                21

<210> SEQ ID NO 10
<211> LENGTH: 19
<212> TYPE: DNA
<213> ORGANISM: Artificial
<220> FEATURE:
<223> OTHER INFORMATION: MxCre primer

<400> SEQUENCE: 10
```
cttgcgaacc tcatcactc                                                          19

<210> SEQ ID NO 11
<211> LENGTH: 20
<212> TYPE: DNA
<213> ORGANISM: Artificial
<220> FEATURE:
<223> OTHER INFORMATION: c-Myc primer

<400> SEQUENCE: 11 tttctttcc gattgctgac                                                          20

<210> SEQ ID NO 12
<211> LENGTH: 20
<212> TYPE: DNA
<213> ORGANISM: Artificial
<220> FEATURE:
<223> OTHER INFORMATION: c-Myc primer

<400> SEQUENCE: 12
taagaagttg ctattttggc                                                         20

<210> SEQ ID NO 13
<211> LENGTH: 22
<212> TYPE: DNA
<213> ORGANISM: Artificial
<220> FEATURE:
<223> OTHER INFORMATION: c-Myc primer

<400> SEQUENCE: 13
tcgcgcccct gaattgctag ga                                                      22

<210> SEQ ID NO 14
<211> LENGTH: 23
<212> TYPE: DNA
<213> ORGANISM: Artificial
<220> FEATURE:
<223> OTHER INFORMATION: c-Myc primer

<400> SEQUENCE: 14
ccgaccgggt ccgagtccct att                                                     23

<210> SEQ ID NO 15
<211> LENGTH: 20
<212> TYPE: DNA
<213> ORGANISM: Artificial
<220> FEATURE:
<223> OTHER INFORMATION: p53 primer

<400> SEQUENCE: 15
acagcgtggt ggtaccttat                                                         20

<210> SEQ ID NO 16
<211> LENGTH: 18
<212> TYPE: DNA
<213> ORGANISM: Artificial
<220> FEATURE:
<223> OTHER INFORMATION: p53 primer

<400> SEQUENCE: 16
tatactcaga gccggcct                                                           18

<210> SEQ ID NO 17
<211> LENGTH: 20
<212> TYPE: DNA

```
<213> ORGANISM: Artificial
<220> FEATURE:
<223> OTHER INFORMATION: p53 primer

<400> SEQUENCE: 17
ctatcaggac atagcgttgg                                              20

<210> SEQ ID NO 18
<211> LENGTH: 18
<212> TYPE: DNA
<213> ORGANISM: Artificial
<220> FEATURE:
<223> OTHER INFORMATION: Puma primer

<400> SEQUENCE: 18
gcggcggaga caagaaga                                                18

<210> SEQ ID NO 19
<211> LENGTH: 26
<212> TYPE: DNA
<213> ORGANISM: Artificial
<220> FEATURE:
<223> OTHER INFORMATION: Puma primer

<400> SEQUENCE: 19
agtcccatga agagattgta catgac                                       26

<210> SEQ ID NO 20
<211> LENGTH: 19
<212> TYPE: DNA
<213> ORGANISM: Artificial
<220> FEATURE:
<223> OTHER INFORMATION: p21 primer

<400> SEQUENCE: 20
ttccgcacag gagcaaagt                                               19

<210> SEQ ID NO 21
<211> LENGTH: 17
<212> TYPE: DNA
<213> ORGANISM: Artificial
<220> FEATURE:
<223> OTHER INFORMATION: p21 primer

<400> SEQUENCE: 21
cggcgcaact gctcact                                                 17

<210> SEQ ID NO 22
<211> LENGTH: 21
<212> TYPE: DNA
<213> ORGANISM: Artificial
<220> FEATURE:
<223> OTHER INFORMATION: Bax primer

<400> SEQUENCE: 22
tggagctgca gaggatgatt g                                            21

<210> SEQ ID NO 23
<211> LENGTH: 17
<212> TYPE: DNA
<213> ORGANISM: Artificial
<220> FEATURE:
<223> OTHER INFORMATION: Bax primer

<400> SEQUENCE: 23
agctgccacc cggaaga                                                 17
```

```
<210> SEQ ID NO 24
<211> LENGTH: 20
<212> TYPE: DNA
<213> ORGANISM: Artificial
<220> FEATURE:
<223> OTHER INFORMATION: FBW7 primer

<400> SEQUENCE: 24
gtgatagagc cccagttcca                                               20

<210> SEQ ID NO 25
<211> LENGTH: 20
<212> TYPE: DNA
<213> ORGANISM: Artificial
<220> FEATURE:
<223> OTHER INFORMATION: FBW7 primer

<400> SEQUENCE: 25
cctcagccaa aattctccag                                               20

<210> SEQ ID NO 26
<211> LENGTH: 21
<212> TYPE: DNA
<213> ORGANISM: Artificial
<220> FEATURE:
<223> OTHER INFORMATION: c-Myc primer

<400> SEQUENCE: 26
cttctctcct tcctcggact c                                             21

<210> SEQ ID NO 27
<211> LENGTH: 24
<212> TYPE: DNA
<213> ORGANISM: Artificial
<220> FEATURE:
<223> OTHER INFORMATION: c-Myc primer

<400> SEQUENCE: 27
ggagatgagc ccgactccga cctc                                          24

<210> SEQ ID NO 28
<211> LENGTH: 20
<212> TYPE: DNA
<213> ORGANISM: Artificial
<220> FEATURE:
<223> OTHER INFORMATION: FBW7 primer

<400> SEQUENCE: 28
gtgatagaac cccagtttca                                               20

<210> SEQ ID NO 29
<211> LENGTH: 20
<212> TYPE: DNA
<213> ORGANISM: Artificial
<220> FEATURE:
<223> OTHER INFORMATION: FBW7 primer

<400> SEQUENCE: 29
cttcagccaa aattctccag                                               20

<210> SEQ ID NO 30
<211> LENGTH: 20
<212> TYPE: DNA
<213> ORGANISM: Artificial
<220> FEATURE:
```

```
<223> OTHER INFORMATION: c-Myc primer

<400> SEQUENCE: 30
gctgcttaga cgctggattt                                               20

<210> SEQ ID NO 31
<211> LENGTH: 21
<212> TYPE: DNA
<213> ORGANISM: Artificial
<220> FEATURE:
<223> OTHER INFORMATION: c-Myc primer

<400> SEQUENCE: 31
cgaggtcata gttcctgttg g                                             21

<210> SEQ ID NO 32
<211> LENGTH: 20
<212> TYPE: DNA
<213> ORGANISM: Artificial
<220> FEATURE:
<223> OTHER INFORMATION: GAPDH primer

<400> SEQUENCE: 32
cttttgcgtc gccagccgag                                               20

<210> SEQ ID NO 33
<211> LENGTH: 20
<212> TYPE: DNA
<213> ORGANISM: Artificial
<220> FEATURE:
<223> OTHER INFORMATION: GAPDH primer

<400> SEQUENCE: 33
ccaggcgccc aatacgacca                                               20
```

INHIBITION OF C-MYC UBIQUITINATION TO PREVENT CANCER INITIATION AND PROGRESSION

This application is a national stage application under 35 U.S.C. 371 from PCT Application No. PCT/US2012/062388, filed Oct. 29, 2012, which claims the benefit of U.S. Provisional Patent Application Ser. No. 61/552,315, filed Oct. 27, 2011, both of which are hereby incorporated by reference in their entirety.

This invention was made with government support under grant numbers R01CA133379, R01CA105129, R21CA141399, R01CA149655, and R01GM088847 awarded by the National Institutes of Health. The government has certain rights in this invention.

FIELD OF THE INVENTION

The present invention relates to methods for inhibiting c-Myc ubiquitination in cancerous cell populations responsible for disease initiation and progression.

BACKGROUND OF THE INVENTION

Chronic myeloid leukemia (CML) was the first cancer for which a specific genetic abnormality was identified, the Philadelphia chromosome (Nowell & Hungerford, "Chromosome Studies on Normal and Leukemic Human Leukocytes," *J. Nat'l. Cancer Inst.* 25:85-109 (1960)). Subsequent studies identified that the translocation event occurred between t(9; 22)(q34;q11), which fused the breakpoint cluster region gene (BCR) with the Abelson kinase (ABL1) gene to produce the oncogene, Bcr-Abl (Bartram et al., "Translocation of C-abl Oncogene Correlates with the Presence of a Philadelphia Chromosome in Chronic Myelocytic Leukaemia," *Nature* 306:277-280 (1983); Druker, B. J., "Translation of the Philadelphia Chromosome Into Therapy for CML," *Blood* 112: 4808-4817 (2008); Rowley, J. D., "Letter: A New Consistent Chromosomal Abnormality in Chronic Myelogenous Leukaemia Identified by Quinacrine Fluorescence and Giemsa Staining," *Nature* 243:290-293 (1973)). This fusion protein possesses constitutive tyrosine kinase activity resulting in development of myeloid leukemia through aberrant differentiation of hematopoietic stem cells (HSC) towards the myeloid lineage. Clinically, CML progresses through at least three different phases: chronic phase (CP), late chronic/accelerated phase (AP) and blast crisis (BC), respectively.

Patients diagnosed with CML in the early chronic phase have been successfully treated with imatinib, which inhibits the tyrosine kinase activity of Bcr-Abl and have a 5-year progression free survival rate of 89% (Druker et al., "Five-Year Follow-Up of Patients Receiving Imatinib for Chronic Myeloid Leukemia," *N. Engl. J. Med.* 355:2408-2417 (2006)). However, only a fraction of imatinib-treated patients achieve long-term remission, suggesting that the compound is unable to target CML initiating populations (de Lavallade et al., "Imatinib for Newly Diagnosed Patients With Chronic Myeloid Leukemia: Incidence of Sustained Responses in an Intention-to-Treat Analysis," *J. Clin. Oncol.* 26:3358-3363 (2008); Hochhaus et al., "Six-Year Follow-Up of Patients Receiving Imatinib for the First-Line Treatment of Chronic Myeloid Leukemia," *Leukemia* 23:1054-1061 (2009)). Indeed, the majority of the patients relapse upon cessation of tyrosine-kinase inhibitor (TKI) treatment (Michor et al., "Dynamics of Chronic Myeloid Leukaemia," *Nature* 435: 1267-1270 (2005)). Moreover, some patients, particularly the ones that present with advanced disease can develop resistance to Imatinib treatment (O'Hare et al., "Targeted CML Therapy: Controlling Drug Resistance, Seeking Cure," *Curr. Opin. Genet. Dev.* 16:92-99 (2006)). The mechanisms thought to drive resistance and disease relapse include the acquisition of mutations in the kinase domain of Bcr-Abl, amplification of Bcr-Abl, and clonal evolution (Gorre et al., "Clinical Resistance to STI-571 Cancer Therapy Caused by BCR-ABL Gene Mutation or Amplification," *Science* 293: 876-880 (2001); Jabbour et al., "Frequency and Clinical Significance of BCR-ABL Mutations in Patients With Chronic Myeloid Leukemia Treated With Imatinib Mesylate," *Leukemia* 20:1767-1773 (2006); le Coutre et al., "Induction of Resistance to the Abelson Inhibitor STI571 in Human Leukemic Cells Through Gene Amplification," *Blood* 95:1758-1766 (2000); Shah et al., "Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia," *Cancer Cell* 2:117-125 (2002)).

An increasing body of work has suggested that disease relapse upon cessation of TKI therapy could be due to a rare population of leukemia initiating cells (LICs) that are resistant or refractory to treatment (Bhatia et al., "Persistence of Malignant Hematopoietic Progenitors in Chronic Myelogenous Leukemia Patients in Complete Cytogenetic Remission Following Imatinib Mesylate Treatment," *Blood* 101: 4701-4707 (2003); Corbin et al., "Human Chronic Myeloid Leukemia Stem Cells are Insensitive to Imatinib Despite Inhibition of BCR-ABL Activity," *J. Clin. Invest.* 121:396-409 (2011); Graham et al., "Primitive, Quiescent, Philadelphia-Positive Stem Cells From Patients With Chronic Myeloid Leukemia are Insensitive to STI571 In Vitro," *Blood* 99:319-325 (2002); Hu et al., "beta-Catenin is Essential for Survival of Leukemic Stem Cells Insensitive to Kinase Inhibition in Mice with BCR-ABL-Induced Chronic Myeloid Leukemia," *Leukemia* 23:109-116 (2009)). LICs are thought to possess properties similar to normal hematopoietic stem cells such as self-renewal, quiescence and resistance to traditional chemotherapy (Bonnet & Dick, "Human Acute Myeloid Leukemia is Organized as a Hierarchy That Originates From a Primitive Hematopoietic Cell," *Nat. Med.* 3:730-737 (1997); Huntly & Gilliland, "Leukaemia Stem Cells and the Evolution of Cancer-Stem-Cell Research," *Nat. Rev. Cancer* 5:311-321 (2005)). Thus, the LIC subset might act as a reservoir contributing to relapse by passing Bcr-Abl on to its progeny, which then mimic the disease. In different types of leukemia, evidence in support of the LIC determined that only a small fraction of acute myeloid leukemia cells from patients were able to recapitulate the disease when transplanted into immuno-compromised animals (Bonnet & Dick, "Human Acute Myeloid Leukemia is Organized as a Hierarchy That Originates From a Primitive Hematopoietic Cell," *Nat. Med.* 3:730-737 (1997); Lapidot et al., "A Cell Initiating Human Acute Myeloid Leukaemia After Transplantation Into SCID Mice," *Nature* 367:645-648 (1994)). Using similar assays, putative LIC populations were also identified in patients diagnosed with chronic phase and blast crisis CML (Jamieson et al., "Granulocyte-Macrophage Progenitors as Candidate Leukemic Stem Cells In Blast-Crisis CML," *N. Engl. J. Med.* 351:657-667 (2004); Sirard et al., "Normal and Leukemic SCID-Repopulating Cells (SRC) Coexist in the Bone Marrow and Peripheral Blood From CML Patients in Chronic Phase, Whereas Leukemic SRC are Detected in Blast Crisis," *Blood* 87:1539-1548 (1996); Wang et al., "High Level Engraftment of NOD/SCID Mice by Primitive Normal and Leukemic Hematopoietic Cells From Patients With Chronic Myeloid Leukemia in Chronic Phase," *Blood* 91:2406-2414 (1998)).

The development of mouse models, which proved that expression of Bcr-Abl alone is indeed leukemogenic, have provided an important tool to investigate the mechanisms involved in maintaining the LIC subset (Daley et al., "Induction of Chronic Myelogenous Leukemia in Mice by the P210bcr/abl Gene of the Philadelphia Chromosome," *Science* 247:824-830 (1990); Heisterkamp et al., "Acute Leukaemia in bcr/abl Transgenic Mice," *Nature* 344:251-253 (1990); Pear et al., "Efficient and Rapid Induction of a Chronic Myelogenous Leukemia-Like Myeloproliferative Disease in Mice Receiving P210 bcr/abl-Transduced Bone Marrow," *Blood* 92:3780-3792 (1998)). Over the years, the Bcr-Abl oncogene has been shown to contribute to tumorigenesis through deregulation of molecular pathways that control hematopoietic stem cell self-renewal and differentiation (Heidel et al., "Genetic and Pharmacologic Inhibition of Beta-Catenin Targets Imatinib-Resistant Leukemia Stem Cells in CML," *Cell Stem Cell* 10:412-424 (2012); Jamieson et al., "Granulocyte-Macrophage Progenitors as Candidate Leukemic Stem Cells In Blast-Crisis CML," *N. Engl. J. Med.* 351:657-667 (2004); Nakahara et al., "Hes1 Immortalizes Committed Progenitors and Plays a Role in Blast Crisis Transition in Chronic Myelogenous Leukemia," *Blood* 115:2872-2881 (2010); Passegue et al., "JunB Deficiency Leads to a Myeloproliferative Disorder Arising From Hematopoietic Stem Cells," *Cell* 119: 431-443 (2004); Zhao et al., "Loss of Beta-Catenin Impairs the Renewal of Normal and CML Stem Cells In Vivo," *Cancer Cell* 12:528-541 (2007); Zhao et al., "Hedgehog Signalling is Essential for Maintenance of Cancer Stem Cells in Myeloid Leukaemia," *Nature* 458:776-779 (2009). Moreover, transplantation studies in mouse models of Bcr-Abl-induced chronic phase CML suggested that LIC activity is confined to Bcr-Abl-expressing $Lin^{neg}Sca1^+c$-$Kit^+$ (LSK) cells (Neering et al., "Leukemia Stem Cells in a Genetically Defined Murine Model of Blast-Crisis CML," *Blood* 110: 2578-2585 (2007)).

SUMMARY OF THE INVENTION

A first aspect of the present invention is directed to a method of inhibiting cancer cell proliferation, differentiation and/or survival. This method involves administering to a population of cancer cells a Fbw7 inhibitor under conditions effective to inhibit cancer cell proliferation, differentiation, and/or survival.

Another aspect of the present invention relates to a method of inhibiting leukemic initiating cell proliferation, differentiation and/or survival. This method involves administering to a population of leukemic initiating cells a c-Myc inhibitor or a GSK3 inhibitor under conditions effective to inhibit leukemic initiation cell proliferation, differentiation, and/or survival.

Another aspect of the present invention relates to a method of preventing or treating cancer in a subject. This method involves selecting a subject having cancer or at risk of developing cancer and administering a Fbw7 inhibitor to the selected subject under conditions effective to prevent or treat cancer in the subject.

Another aspect of the present invention is directed to a method of preventing or treating chronic myeloid leukemia in a subject. This method involves selecting a subject having chronic myeloid leukemia or at risk of developing chronic myeloid leukemia and administering a c-Myc inhibitor or GSK3 inhibitor to the selected subject under conditions effective to prevent or treat chronic myeloid leukemia in the subject.

Fbw7, an E3 ubiquitin ligase, is a member of the Cullin-1/SCF complex serving as the substrate recognition component, which targets specific proteins for degradation by the 26S proteasome. Fbw7 has been shown to regulate a number of oncogenes such as c-Myc, Notch, and cyclinE (Gupta-Rossi et al., "Functional Interaction Between SEL-10, an F-Box Protein, and the Nuclear Form of Activated Notch1 Receptor," *J. Biol. Chem.* 276:34371-34378 (2001); Hubbard et al., "sel-10, a Negative Regulator of Lin-12 Activity in *Caenorhabditis elegans*, Encodes a Member of the CDC4 Family of Proteins," *Genes Dev.* 11:3182-3193 (1997); Inuzuka et al., "SCF(FBW7) Regulates Cellular Apoptosis by Targeting MCL1 for Ubiquitylation and Destruction," *Nature* 471:104-109 (2011); Koepp et al., "Phosphorylation-Dependent Ubiquitination of Cyclin E by the SCFFbw7 Ubiquitin Ligase," *Science* 294:173-177 (2001); Moberg et al., "Archipelago Regulates Cyclin E Levels in *Drosophila* and is Mutated in Human Cancer Cell Lines," *Nature* 413:311-316 (2001); Oberg et al., "The Notch Intracellular Domain is Ubiquitinated and Negatively Regulated by the Mammalian Sel-10 Homolog," *J. Biol. Chem.* 276:35847-35853 (2001); Strohmaier et al., "Human F-Box Protein hCdc4 Targets Cyclin E for Proteolysis and is Mutated in a Breast Cancer Cell Line," *Nature* 413:316-322 (2001); Welcker et al., "A Nucleolar Isoform of the Fbw7 Ubiquitin Ligase Regulates c-Myc and Cell Size," *Curr. Biol.* 14:1852-1857 (2004); Welcker et al., "The Fbw7 Tumor Suppressor Regulates Glycogen Synthase Kinase 3 Phosphorylation-Dependent c-Myc Protein Degradation," *P. Nat'l. Acad. Sci. U.S.A.* 101:9085-9090 (2004); Yada et al., "Phosphorylation-Dependent Degradation of c-Myc is Mediated by the F-Box Protein Fbw7," *Embo J.* 23:2116-2125 (2004), which are hereby incorporated by reference in their entirety). Fbw7 is also essential for the maintenance of adult HSC quiescence (Matsuoka et al., "Fbxw7 Acts as a Critical Fail-Safe Against Premature Loss of Hematopoietic Stem Cells and Development of T-ALL," *Genes Dev.* 22(8):986-91 (2008); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety). Deletion of Fbw7 in HSCs leads to c-Myc accumulation, aberrant cell cycle entry and eventual HSC exhaustion (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety).

As demonstrated herein, Fbw7 is essential for maintenance of the leukemia initiating cell (LIC) population, and subsequent development of lethal CML. Fbw7 deficient LICs could neither propagate in vitro nor transfer disease in vivo. Loss of Fbw7 expression led to a rapid decrease in circulating tumor cells, minimized spleen size, reduced leukemic cell infiltration into peripheral tissues, and caused a significant reduction of LIC activity leading to the survival of recipient animals. Mechanistically, Fbw7 deletion led to oncogene (c-Myc)-induced LIC death that could be rescued by either decreasing c-Myc protein levels or inhibition of the p53 response. The relative abundance of c-Myc protein expression in established CML is crucial for disease propagation in a mouse model of CML. Taken together, this work indicates that Fbw7-regulated ubiquitination controls relative levels of c-Myc protein abundance and is essential for both initiation and progression of CML. Because c-Myc activity drives a number of distinct tumor types, Fbw7 inhibition is a viable therapeutic approach for a wide range of blood and solid tumors.

BRIEF DESCRIPTION OF THE DRAWINGS

FIG. 1A is a graph showing the average colony number from VavCre$^+$Fbw7$^{+/+}$ and VavCre$^+$Fbw7$^{-/-}$ cells infected with Bcr-Abl expressing retrovirus at the first plating. Images on right are representative colonies from control or Fbw7$^{-/-}$ plated Bcr-Abl$^+$ Lin$^{neg}$Sca1$^+$c-Kit$^+$ (LSKs). Error bars indicate Standard deviation (StD). *** p<0.0001. FIGS. 1B-1C show FACS analysis (FIG. 1B) and blood smears (FIG. 1C) of peripheral blood taken from host mice transplanted with VavCre$^+$Fbw7$^{+/+}$ (Control) or VavCre$^+$Fbw7$^{-/-}$ Bcr-Abl$^+$ LSK cells (n=5 for each genotype). FIG. 1D is a Kaplan Meier survival curve of irradiated animals that were transplanted with either VavCre$^+$Fbw7$^{+/+}$ (-■-) or VavCre$^+$Fbw7$^{-/-}$ Bcr-Abl$^+$ LSKs (-♦-). (n=5, for each genotype).

FIG. 2A is a graph showing the average colony-forming units from sort purified CD150$^+$ LSKs sorted from either VavCre$^+$ Fbw7$^{+/+}$ or VavCre+Fbw7$^{-/-}$ mice. FIG. 2B is a FACS analysis showing percentage of Lin$^-$ cells from the bone marrow of VavCre$^+$ Fbw7$^{+/+}$ or VavCre$^+$Fbw7$^{-/-}$ mice. FIG. 2C is a FACS analysis gated on Lin$^-$ and stained with c-kit and Sca-1 from 2 week old VavCre$^+$ Fbw7$^{+/+}$ or VavCre$^+$Fbw7$^{-/-}$ mice. N=3 mice for each genotype. FIG. 2D is a graph showing QRT-PCR analysis of Fbw7 expression in sorted LSK from Wt mice or Bcr-Abl$^+$ LSK. Error bars indicate standard deviation (StD). FIGS. 2E-2F show a FACS plots (FIG. 2E) and graph (FIG. 2F) show percentage of CD45.2 (either VavCre+ Fbw7$^{+/+}$ or VavCre$^+$Fbw7$^{-/-}$) cells in the BM of irradiated CD45.1 mice 24 hours after transplantation. N=5 mice from each genotype. Error bars indicate standard deviation (StD).

FIG. 3A is a FACS analysis of peripheral blood from mice transplanted with MxCre$^+$Fbw7$^{+/+}$ and MxCre$^+$Fbw7$^{-/-}$ Bcr-Abl infected LSK cells. FIG. 3A, upper panel: pre-polyI-polyC treatment. FIG. 3B, lower panel: post-polyI-polyC treatment. The graph on right is a quantification of Bcr-Abl expressing cells in the peripheral blood. FIG. 3B is a graph showing QRT-PCR analysis of Fbw7 expression in sorted populations from WT and Fbw7$^{-/-}$ murine CML tumors 5 days from the post poly (I:C) injection. Error bars indicate standard deviation (StD). * p<0.01, ** p<0.001. FIG. 3C shows FACS analysis of the bone marrow from MxCre$^+$Fbw7$^{+/+}$ and MxCre$^+$Fbw7$^{-/-}$ (5 and 10 days post deletion, respectively) animals transplanted with Bcr-Abl$^+$ LSK cells. FIG. 3D are blood smears of MxCre$^+$Fbw7$^{+/+}$ and MxCre$^+$Fbw7$^{-/-}$ mice approximately 10 days post polyI-polyC injections. FIG. 3E shows hematoxylin and eosin (H&E) staining of secondary tissues (i.e., liver and lung) from MxCre$^+$Fbw7$^{+/+}$ and MxCre$^+$Fbw7$^{-/-}$ animals. FIG. 3F shows Kaplan Meier survival curves of irradiated animals that were transplanted with either Fbw7$^{+/+}$ and Fbw7$^{-/-}$ Bcr-Abl$^+$ LSKs. (n=9, for each genotype).

FIG. 4A is a FACS analysis and FIG. 4B shows peripheral blood smears taken from secondary recipient mice receiving equal numbers of Bcr-Abl$^+$ LSK cells from spleens of either MxCre$^+$ Fbw7$^{+/+}$ or MxCre$^+$Fbw7$^{-/-}$ animals (n=4 for each genotype). FIG. 4C is a FACs analysis of peripheral blood from MxCre$^+$Fbw7$^{+/+}$ and MxCre$^+$Fbw7$^{-/-}$ secondary recipient mice showing the lineage markers CD11b$^+$ (myeloid) and B220$^+$ (B-lymphoid). FIG. 4D shows H&E staining of secondary tissues (i.e., liver and lung) in MxCre$^+$Fbw7$^{+/+}$ and MxCre$^+$Fbw7$^{-/-}$ secondary recipient animals. FIG. 4E is a Kaplan Meier survival curve of secondary recipient mice which received MxCre$^+$Fbw7$^{+/+}$ or MxCre$^+$Fbw7$^{-/-}$ Bcr-Abl$^+$ (normalized to LSK number) cells from the spleen of primary recipient animals. Error bars indicate Standard deviation (StD).

FIG. 5A shows FACS plots depicting the relative percentage of Bcr-Abl expressing stem and progenitor cells in the bone marrow of MxCre$^+$Fbw7$^{+/+}$ or MxCre$^+$Fbw7$^{-/-}$ mice. The graph on right of FIG. 5A depicts total number of tumor stem and progenitor cells. FIG. 5B shows FACS plots of the relative annexin and 7-AAD positive cells in the Bcr-Abl$^+$ LSK subset in the bone marrow of MxCre$^+$Fbw7$^{+/+}$ or MxCre$^+$Fbw7$^{-/-}$ animals. The graph on right of FIG. 5B represents percent of annexin V positive cells in the Bcr-Abl$^+$ LSK of both cohorts. The graphs of FIG. 5C show expression of the p53 target genes, Puma, Bax, and p21 by QT-PCR analysis, in sorted control or Fbw7$^{-/-}$ LSKs from the tumor. Error bars indicate Standard deviation (StD). n=4 for each genotype; * p<0.05, ** p<0.01.

FIG. 6A shows the QRT-PCR analysis of c-Myc expression in sorted tumor subsets (LSK, cKit$^+$ and Lin$^+$). FIG. 6B shows c-Myc protein expression in normal and tumor (Bcr-Abl$^+$) LSK cells in the bone marrow. The graph of FIG. 6B shows mean fluorescence intensity (MFI) for eGFP (c-Myc protein) in control (WT) and tumor LSK subsets. FIG. 6C is a western blot analysis of c-Myc protein expression in LSKs sorted from WT tumor, WT Fbw7$^{-/-}$ and WT mice. FIG. 6D shows c-Myc protein expression in MxCre$^+$Fbw7$^{+/+}$ or MxCre$^+$Fbw7$^{-/-}$ Bcr-Abl$^+$ LSK. FIG. 6E shows the average colony number from sort purified Bcr-Abl$^+$ LSK cells from MxCre$^+$Fbw7$^{+/+}$, MxCre$^+$ Fbw7$^{-/-}$, or MxCre$^+$Fbw7$^{-/-}$ Myc$^{+/-}$, and FIG. 6F shows the same from MxCre$^+$Fbw7$^{+/+}$ or MxCre$^+$Fbw7$^{-/-}$ shp53 mice. FIG. 6G is a graph showing the number of colonies from secondary replatings. FIG. 6H show images of colonies generated from the different Bcr-Abl$^+$ genotypes (n=3 for each genotype). FIG. 6I is a Kaplan Meier survival curve for animals transplanted with control (red line), Fbw7$^{-/-}$ Myc$^{+/-}$ (blue line) LSKs transduced with a retrovirus expressing Bcr-Abl, or Fbw7$^{-/-}$ LSKs transduced with a retrovirus expressing Bcr-Abl and a shRNA targeting p53 (green). Error bars indicate Standard deviation (StD). *p<0.01, **p<0.001.

FIG. 7A is a western blot analysis of Bcr, cleaved-Notch-1 and -actin protein in WT and Fbw7$^{-/-}$ Bcr-Abl$^+$ total ckit$^+$ cells. FIGS. 7B and 7C show the results of FACS analysis of BM derived LSKs (FIG. 7B) and the frequency of CD150 CD48 populations in Control, MxCre$^+$Fbw7$^{-/-}$ and Mx$^-$Cre$^+$Fbw7$^{-/-}$ Notch1$^{-/-}$ Notch2$^{+/-}$ mice two weeks after the last polyI-polyC treatment (FIG. 7C). FIG. 7D shows the cell cycle status of LSK cells in Control, MxCre$^+$Fbw7$^{-/-}$ and Mx-Cre$^+$Fbw7$^{-/-}$ Notch1$^{-/-}$ Notch2$^{+/-}$ mice as determined with DAPI staining and assessed by FACS analysis. FIG. 7E is a graph showing average colony number in CFU assay. Error bars indicate standard deviation (Std) of N=4 mice.

FIGS. 8A and 8B show the deletion of Fbw7 and Myc alleles presented post polyI:polyC injections presented in FIG. 6. FIG. 8C shows the deletion of Fbw7 allele in recipient mice transplanted with Fbw7$^{-/-}$ LSKs transduced with a retrovirus expressing Bcr-Abl and a shRNA targeting p53 post polyI: polyC injections presented in FIG. 6.

FIG. 9A shows c-Myc protein expression in Bcr-Abl$^+$ CML tumor subsets. The upper left panel of FIG. 9A shows c-Myc expression in CML tumor populations. The upper right panel for FIG. 9A show c-Myc expression in Bcr-Abl$^+$ CD11b$^+$ GR1$^+$ cells. The lower left panel of FIG. 9A shows c-Myc expression in Bcr-Abl$^+$ myeloid progenitor subset, and the lower right panel shows c-Myc expression in Bcr-Abl$^+$ LSK stem and progenitor cells. FIG. 9B shows a peripheral blood analysis of mice that received Bcr-Abl infected LSKs from MxCre$^+$c-Myc$^{w/w}$ and MxCre$^+$c-Myc$^{f/f}$ mice. The upper panel of FIG. 9B show pre-polyI-polyC treatment, and the lower panel shows post-polyI-polyC treatment. FIG. 9C depicts H&E staining of secondary tissues (liver and lung) from mice transplanted with c-Myc$^{+/+}$ and c-Myc$^{-/-}$ Bcr-Abl$^+$ LSKs. FIG. 9D is a Kaplan Meier survival curve (n=5). Error bars indicate Standard deviation (StD).

FIG. 10A depicts the use of a FACS sort to isolate Bcr-Abl$^+$ lineage$^+$, Bcr-Abl$^+$ c-kit$^+$, and Bcr-Abl$^+$ cMyc-GFP$^+$ LSK. The three cell populations were then transplanted into lethally irradiated recipients, and peripheral blood (PB) samples were analyzed at day 12 and 20 to determine % of Bcr-Abl$^+$ cells (FIG. 10B). FIG. 10C shows the proportion of recipient mice that developed lethal CML.

FIG. 11A shows the average CFU from MxCre$^+$c-Myc$^{+/+}$ and MxCre$^+$c-Myc$^{+/-}$ cells infected with Bcr-Abl expressing retrovirus. Left bar graph of FIG. 11A shows primary plating, and right bar graph of FIG. 11A shows secondary plating. Images of FIG. 11A are representative colonies from control or c-Myc$^{+/-}$ plated Bcr-Abl$^+$ LSKs. Error bars indicate StD. FIG. 11B shows the genotyping PCR results from recipient BM depicting deleted allele. FIG. 11C (left panel) shows FACS analysis of PB at day 14 post-transplantation of recipient mice. FIG. 11C (right panel) shows lineage markers, Gr1 (myeloid) and B220 (B-lymphoid) gated on Bcr-Abl$^+$ cells. FIG. 11D is a blood smear of MxCre$^+$c-Myc$^{+/-}$ mice approximately 20 days post transplantation stained with Wright-Giemsa. FIG. 11E shows H&E staining of secondary tissues (i.e., liver and lung) in MxCre$^+$c-Myc$^{+/-}$ recipient animals.

FIG. 12A is a FACS analysis of PB from mice transplanted with MxCre$^+$Fbw7$^{+/+}$ and MxCre$^+$Fbw7$^{-/-}$ Bcr-Abl infected total BM cells. The upper panel of FIG. 12A shows the analysis at 12 days post-transplant prior to polyI-polyC treatment. The lower panels of FIG. 12A show the analysis at 21 days (middle panel) and 28 days (bottom panel) post-polyI-polyC treatment. Panel on right is a quantification of Bcr-Abl expressing cells in the PB. FIG. 12B is a graph showing the percent of Bcr-Abl$^+$ B220$^+$ cells in the PB of both cohorts. FIG. 12C shows genotyping PCR results from recipient BM depicting deleted allele. FIG. 12D shows H&E staining of secondary tissues (i.e., spleen and lung) in MxCre$^+$Fbw7$^{+/+}$ and MxCre$^+$Fbw7$^{-/-}$ recipient animals. FIG. 12E are images of spleens taken from MxCre$^+$Fbw7$^{+/+}$ and MxCre$^+$Fbw7$^{-/-}$ recipient animals at day 28. FIG. 12F shows the QRT-PCR analysis of Fbw7 and c-Myc expression in sorted tumor. FIG. 12G shows c-Myc protein expression in spleen of MxCre$^+$Fbw7$^{+/+}$ and MxCre$^+$Fbw7$^{-/-}$ recipient animals gated on B220+. The FACS plots of FIG. 12H show Annexin V and 7-AAD positive cells in the BCR-ABL$^+$ B220$^+$ cell fraction of bone marrow from MxCre$^+$Fbw7$^{+/+}$ or MxCre$^+$Fbw7$^{-/-}$ recipient animals. FIG. 12I shows a QRT-PCR analysis p53 target gene expression, including Puma, Bim, and Noxa expression, in sorted control or Fbw7$^{-/-}$ tumors. Error bars indicate Standard deviation (StD).

FIGS. 13A and 13B show expression of FBW7 and c-MYC from total peripheral blood mononuclear cells (PBMNCs) in normal or patient samples in chronic phase (CP) CML, CP patients currently treated with imatinib and blast crisis (BC) phase. FIG. 13A shows the results of qRT-PCR analysis *p<0.01, and FIG. 13B shows the results of western blot analysis. The FACS plots of FIG. 13C show CD45 and CD34 expression in human CML patients used to sort stem and progenitor populations (CD34$^+$CD38$^+$ and CD34$^+$CD38$^{low}$). FIG. 13D shows qRT-PCR for c-MYC and FBW7 from CD34$^+$CD38$^+$ and CD34$^+$CD38$^{low}$ populations from BM samples taken from patients in CP and BC phase normalized to normal umbilical cord blood (UCB) derived CD34$^+$CD38$^{low}$ *p<0.01. FIG. 13E shows colony formation by CD34$^+$Lin$^-$ cells (from CML patients) transfected with Fbxw7 siRNAs. In FIG. 13F, bone marrow cells from CML patients were transfected with a control siRNA or one of two independent Fbxw7 siRNAs (KD#1 or KD#2) by electroporation, and the CD34$^+$Lin$^-$ fraction was then sorted and cultured on OP-9 cells. The proportion of apoptotic cells among CD34$^+$Lin$^-$ cells was determined by staining with annexin V. FIG. 13G shows intracellular FACS for c-Myc protein in normal UCB derived CD34+ transduced with Bcr-Abl retrovirus and lentivirus expressing either NonTarget (control) or shRNAs against Fbw7. FIG. 13H is a schematic illustrating proposed dosage requirement of c-Myc protein to establish Bcr-Abl dependent CML.

FIGS. 14A-14C show the KU812, CML cell line, following silencing of Fbw7. FIG. 14A is the QRT-PCR analysis of c-Myc and FBW7 expression. FIG. 14B is a bar graph showing relative % of Annexin V$^+$ cells. FIG. 14C is a western blot for c-Myc, Phospho-c-Myc, and Bcr-Abl expression. FIGS. 14D and 14E show normal UCB derived CD34$^+$ cells infected with shRNA against either NonTarget or Fbw7. FIG. 14D shows the average colony number from normal UCB derived CD34+ cells infected with shRNA against either NonTarget or Fbw7. FIG. 14 E is a western blot for c-Myc in total cell lysate from normal UCB derived CD34$^+$ cells infected with shRNA against either NonTarget or Fbw7.

DETAILED DESCRIPTION OF THE INVENTION

Figures 1A, 1B, 1C, 1D:
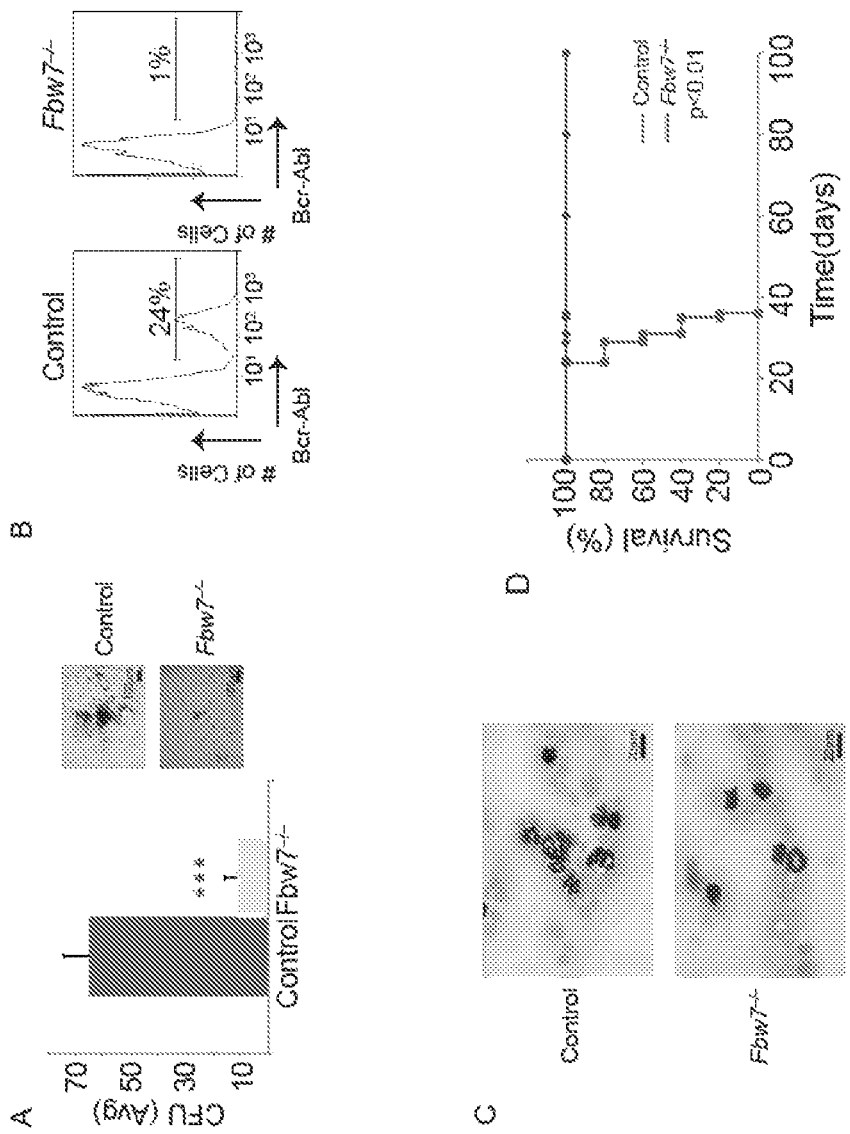
FIGS. 1A-1D show that Fbw7 deletion suppresses initiation of Bcr-Abl-induced chronic myeloid leukemia (CML).

A first aspect of the present invention is directed to a method of inhibiting cancer cell proliferation, differentiation and/or survival. This method involves administering to a population of cancer cells a Fbw7 inhibitor under conditions effective to inhibit cancer cell proliferation, differentiation, and/or survival.

In one embodiment of the present invention, the population of cancer cells is a population of leukemia cells. In particular the population of cells may be chronic myeloid leukemia (CML) cells, acute myeloid leukemia cells, or B-cell acute lymphoblastic leukemia cells. In another embodiment of the present invention, the cancer cells are a subset of leukemic cells known as leukemic initiating cells (LIC). LICs possess properties similar to normal hematopoietic stem cells such as self-renewal, quiescence, and resistance to traditional chemotherapy (Bonnet & Dick, "Human Acute Myeloid Leukemia is Organized as a Hierarchy That Originates From a Primitive Hematopoietic Cell," *Nat. Med.* 3:730-737 (1997); Huntly & Gilliland, "Leukaemia Stem Cells and the Evolution of Cancer-Stem-Cell Research," *Nat. Rev. Cancer* 5:311-321 (2005), which are hereby incorporated by reference in their entirety). As a result, the LIC subset acts as a reservoir of cells contributing to disease relapse. LIC populations have been identified in acute myeloid leukemia, chronic phase and blast crisis CML (Jamieson et al., "Granulocyte-Macrophage Progenitors as Candidate Leukemic Stem Cells In Blast-Crisis CML," *N. Engl. J. Med.* 351:657-667 (2004); Sirard et al., "Normal and Leukemic SCID-Repopulating Cells (SRC) Coexist in the Bone Marrow and Peripheral Blood From CML Patients in Chronic Phase, Whereas Leukemic SRC are Detected in Blast Crisis," *Blood* 87:1539-1548 (1996); Wang et al., "High Level Engraftment of NOD/SCID Mice by Primitive Normal and Leukemic Hematopoietic Cells From Patients With Chronic Myeloid Leukemia in Chronic Phase," *Blood* 91:2406-2414 (1998), which are hereby incorporated by reference in their entirety), pediatric T cell acute lymphoblastic leukemia (T-ALL) (Ma et al., "NOTCH1 Signaling Promotes Human T-Cell Acute Lymphoblastic Leukemia Initiating Cell Regeneration in Supportive Niches," *PLOS One* 7(6): e39725 (2012), which is hereby incorporated by reference in its entirety), adult (T-ALL) (Chiu et al., "Leukemia-initiating Cells in Human T-lymphoblastic Leukemia Exhibit Glucocorticoid Resistance," *Blood* 116: 5268-5279 (2010) which is hereby incorporated by reference), and B-cell acute lymphoblastic leukemia (Castro Alves et al., "Leukemia-initiating Cells of Patient-Derived Acute Lymphoblastic Leukemia Xenografts are Sensitive Toward TRAIL," *Blood* 119 (18):4224-7 (2012), which is hereby incorporated by reference). In accordance with this aspect of the present invention, these and any other known LIC population can be administered a Fbw7 inhibitor to inhibit cell proliferation, differentiation, and/or survival.

Leukemia initiating cells can be identified by their ability to recapitulate disease in animal models and by their cell surface marker expression. Accordingly, in one embodiment of the present invention, the LICs comprise a population of BCR-ABL$^+$CD34$^+$CD38$^-$ cells. In other embodiments, the LICs comprise a population of CD34$^+$CD4$^-$ and CD34$^+$CD7$^-$ cells (pediatric T-ALL), CD7$^+$CD1a$^-$ cells (adult T-ALL), or BCR-ABL$^+$ CD45$^-$CD34$^+$CD38$^-$ cells (CML).

In another embodiment of the present invention, the population of cancer cells are derived from a solid tumor, such as medullablastoma, glioma, or melanoma.

In accordance with this aspect of the present invention, inhibition of cancer cell proliferation, differentiation, and/or survival is achieved using a Fbw7 inhibitor. Fbw7 is an E3 ubiquitin ligase and a member of the Cullin-1/SCF complex. Fbw7 serves as the substrate recognition component of the complex which targets specific proteins for degradation by the 26S proteasome. As described herein, Fbw7 mediated recognition and degradation of certain cancer cell proteins (e.g., c-Myc) regulates the intracellular levels of these proteins so as to maintain cancer cell proliferation, differentiation, and survival. Loss of Fbw7 can disrupt this regulated balance, leading to unphysiologically high levels of cellular protein that lead to cell death. Accordingly, Fbw7 inhibitors of the present invention include those that interact directly or indirectly with Fbw7 to completely or partially inhibit Fbw7 recognition of one or more of its protein substrates in cancer cells. In one embodiment of the present invention, the inhibitor inhibits Fbw7 recognition of c-Myc. Alternatively, Fbw7 inhibitors of the present invention include those that interact directly or indirectly with Fbw7 to completely or partially inhibit Fbw7 binding to the Cullin-1/SCF-complex. Suitable Fbw7 inhibitors of these types include, without limitation, inhibitory peptides, antibodies, and small molecules. Alternatively, the Fbw7 inhibitor interferes with Fbw7 protein expression so as to diminish or abolish the level of Fbw7 protein present in a particular cancer cell. Suitable inhibitors of this type include, without limitation, inhibitor nucleic acid molecules such as RNAi, shRNA, microRNA, and antisense oligonucleotides.

In one embodiment of the present invention, the Fbw7 inhibitor comprises a small molecule biplanar dicarboxylic acid compound, or derivative thereof, such as those described by Aghaj an et al., "Chemical Genetics Screen for Enhancers of Rapamycin Identifies a Specific Inhibitor of an SCF Family E3 Ubiquitin Ligase," *Nat. Biotechnol.* 28:738-742 (2010) and Orlicky et al., "An Allosteric Inhibitor of Substrate Recognition by the SCF(Cdc4) Ubiquitin Ligase," *Nat. Biotechnol.* 28:733-737 (2010), which are hereby incorporated by reference in their entirety. In particular, the Fbw7 inhibitor may comprise 1-(2-carboxynapth-lyl)-2-naphthoic acid (SCF-I2), or a derivative thereof (Orlicky et al., "An Allosteric Inhibitor of Substrate Recognition by the SCF(Cdc4) Ubiquitin Ligase," *Nat. Biotechnol.* 28:733-737 (2010), which are hereby incorporated by reference in their entirety).

In another embodiment of the present invention, the Fbw7 inhibitor comprises a microRNA. MicroRNA (miRNAs) are post-transcriptional regulators that bind complementary sequences on target mRNA transcripts resulting in translational repression or target degradation and gene silencing. One microRNA suitable for achieving Fbw7 silencing and inhibition is microRNA-27a (Lerner et al., "MiRNA-27a Controls FBW7/hCDC4-dependent Cyclin E Degradation and Cell Cycle Progression," *Cell Cycle* 10(13): 2172-83 (2011), which is hereby incorporated by reference in its entirety). The sequence of the mature microRNA-27a (has-miR-27a) is shown as SEQ ID NO: 1 below:

AGGGCUUAGCUGCUUGUGAGCA SEQ ID NO:1

Another suitable microRNA for inhibiting Fbw7 is a microRNA-223 (Kurashige et al., "Overexpression of microRNA-223 Regulates the Ubiquitin Ligase FBXW7 in Oesophageal Squamous Cell Carcinoma," *Br. J. Cancer* 106 (1):182-8 (2012), which is hereby incorporated by reference in its entirety). The sequence of the mature human microRNA-223 (has-miR-223) is shown below as SEQ ID NO: 2.

CGUGUAUUUGACAAGCUGAGUU SEQ ID NO: 2

In another embodiment of the present invention the Fbw7 inhibitor is a Fbw7 siRNA. siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the Fbw7 nucleotide sequence. The mRNA sequence of Fbw7 is known in the art (see NCBI sequence reference numbers NM_033632.3 (transcript variant 1), NM_018315 (transcript variant 2), NM_001013415 (transcript variant 3) and NM_001257069 (transcript variant 4), which are hereby incorporated by reference in their entirety). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. siRNA molecules that effectively interfere with Fbw7 expression are described herein in the Examples and elsewhere (see e.g., Zhao et al., "The Fbw7 Tumor Suppressor Targets KLF5 for Ubiquitin-Mediated Degradation and Suppresses Breast Cell Proliferation," Cancer Research 70:4728 (2010), which is hereby incorporated by reference in its entirety) and are suitable for use in the present invention. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with Fbw7 expression have been described (see e.g., Anzi et al., "Transcriptional Repression of c-Jun's E3 Ubiquitin Ligases Contributes to c-Jun Induction by UV," Cell Signal 20(5):862-71 (2008), which is hereby incorporated by reference in its entirety) and are suitable for use in the methods of the present invention.

In another embodiment of the present invention, the Fbw7 inhibitor is a peptide inhibitor. One suitable Fbw7 peptide/polypeptide inhibitor comprises a peptide or polypeptide derived from the CCAAT/enhancer binding protein-δ (C/EBPδ). C/EBPδ is a transcriptional repressor of Fbw7 (Balamurugan et al., "The Tumour Suppressor C/EBPδ Inhibits FBXW7 Expression and Promotes Mammary Tumour Metastasis," EMBO J. 29:4106-17 (2010), which is hereby incorporated by reference in its entirety). Accordingly, C/EBPδ derived peptides are suitable Fbw7 inhibitors for use in accordance with the methods of the present invention. Other suitable Fbw7 peptide inhibitors that repress Fbw7 transcription are the TRIP-BR decoy peptides described in U.S. Pat. No. 7,223,733 to Hsu (ATGCLLDDG-LEGLFEDID (SEQ ID NO: 3); TGFLTDLTLDDILFADID (SEQ ID NO: 4), which is hereby incorporated by reference in its entirety).

In one embodiment of the present invention, inhibition of cancer cell proliferation, differentiation, and/or cancer cell survival is carried out ex vivo. In an alternative embodiment of the invention, inhibition of cancer cell proliferation, differentiation, and/or survival is carried out in vivo. In accordance with either of these embodiments of the present invention, administration of the Fbw7 inhibitor to the cancer cells can be repeated periodically.

In vivo inhibition of cancer cell proliferation and/or survival is preferably achieved by delivering the Fbw7 inhibitor to only the target cancer cells to avoid systemic inhibition of Fbw7. Methods of targeting Fbw7 inhibitor delivery to different cancer cells are described infra.

Another aspect of the present invention relates to a method of inhibiting leukemic initiating cell proliferation, differentiation and/or survival. This method involves administering to a population of leukemic initiating cells a c-Myc inhibitor or a glycogen synthase kinase-3 (GSK3) inhibitor under conditions effective to inhibit leukemic initiation cell proliferation, differentiation, and/or survival.

As demonstrated herein, a well-defined threshold of c-Myc protein expression is required for the initiation and progression of leukemic disease (e.g., chronic myeloid leukemia and B-cell acute lymphoblastic leukemia) by leukemia initiating cells. Accordingly, agents which inhibit c-Myc expression or agents, such as Fbw7 inhibitors or GSK3 inhibitors, that inhibit c-Myc degradation and result in c-Myc overexpression can be utilized to inhibit leukemic initiating cell proliferation, differentiation, and/or survival.

Leukemia initiating cells can be identified and targeted by their cell surface marker expression. LICs populations comprise BCR-ABL$^+$CD34$^+$CD38$^-$ cells, CD34$^+$CD4$^-$ and CD34$^+$CD7$^-$ cells (pediatric T-ALL), CD7$^+$CD1a$^-$ cells (adult T-ALL), or BCR-ABL$^+$ CD45$^-$CD34$^+$CD38$^-$ cells (CML).

A number of c-Myc inhibitors are known in the art and are suitable for use in the methods of the present invention, including nucleic acid inhibitors, peptide inhibitors and small molecule inhibitors. In particular, suitable c-Myc small molecule inhibitors include, without limitation, 10058-F4, 10009-G9, 10031-B8, 10075-G5, 2RH, #474, 12RH-NCN1, 5360134, and 6525237 (see Prochownik and Vogt, "Therapeutic Targeting of Myc," Genes & Cancer 1(6) 650-659 (2010); Yin et al., "Low Molecular Weight Inhibitors of Myc-Max Interaction and Function," Oncogene 22:6151-59 (2003); and Wang et al., 'Improved Low Molecular Weight Myc-Mas Inhibitors," Mol. Cancer. Ther. 6:2399-408 (2007), which are hereby incorporated by reference in their entirety). A suitable polypeptide inhibitor of c-Myc is the 90 amino acid dominant negative miniprotein known as Omomyc (Savino et al., "The Action Mechanism of the Myc Inhibitor Termed Omomyc May Give Clues on How to Target Myc for Cancer Therapy," PLOS One 6(7):e22284 (2011), which is hereby incorporated by reference in its entirety).

Suitable nucleic acid inhibitors of c-Myc include siRNA, particularly those siRNA molecules targeting the 3'-untranslated region of the c-Myc (see e.g., von Bueren et al., "RNA Interference-Mediated c-Myc Inhibition Prevents Cell Growth and Decreases Sensitivity to Radio- and Chemotherapy in Childhood Medulloblastoma Cells," BMC Cancer 9:10 (2009), which is hereby incorporated by reference in its entirety), c-Myc antisense oligonucleotides (Leonetti et al., "Encapsulation of c-myc Antisense Oligodeoxynucleotides in Lipid Particles Improves Antitumoral Efficacy in Vivo in a Human Melanoma Line," Cancer Gene Ther. 8:459-468 (2001); Akie et al., "A Combination Treatment of c-myc Antisense DNA with All-Trans-Retinoic Acid Inhibits Cell Proliferation by Downregulating c-myc Expression in Small Cell Lung Cancer," Antisense Nucleic Acid Drug Dev. 10:243-249 (2000); Chen et al., "Molecular Therapy with Recombinant Antisense c-myc Adenovirus for Human Gastric Carcinoma Cells in Vitro and in Vivo," J. Gastroenterol. Hepatol. 16:22-28 (2001), which are hereby incorporated by reference in their entirety), c-Myc triple helix forming oligodeoxyribonucleotides (McGuffie et al., "Design of a Novel Triple Helix-Forming Oligodeoxyribonucleotide Directed to the Major Promoter of the c-myc Gene," Nucleic Acids Res. 30:2701-09 (2002), which is hereby incorporated by reference in its entirety), and ribozymes (Cheng et al., "Inhibition of Cell Proliferation in HCC-9204 Hepatoma Cells by a c-myc Specific Ribozyme," Cancer Gene Ther. 7:407-412 (2000), which is hereby incorporated by reference in its entirety).

In accordance with this aspect of the present invention GSK3 inhibitors can also be utilized to inhibit leukemia initiating cell proliferation, differentiation, and/or survival. Fbw7-mediated c-Myc recognition depends on c-Myc phosphorylation by GSK-3. Accordingly, inhibition of GSK-3, in particular, GSK-3β, will inhibit leukemia initiating cell proliferation, differentiation, and/or survival in a manner similar to Fbw7 inhibition. A variety of pharmacological inhibitors of GSK-3 are known in the art and are suitable for use in the methods of the present invention. Suitable GSK-3 inhibitors include, without limitation, Hymenialdisine, Flavopiridol, Kenpaullone, Alsterpaullone, Azakenpaullone, Indirubin-3'-oxime, 6-bromoindirubin-3'-oxime, 6-bomoindirubin-3' acetoxime, Aloisine A, Aloisine B, TDZD8, Compound 12, Pyrazolopyridine 18, Pyrazolopyridine 9, Pyrazolopyridine 34, CHIR98014, CHIR99021, CT20026, Compound 1, SU9516, ARA014418, Staurosporine, Compound 5a, Compound 29, Compound 46, GF109203x, Ro318220, SB216763, SB415286, I5, CGP60474, Compound 8b, TWS119, Compound 1A, Compound 17, Lithium, Beryllium, and Zinc (see Meijer et al., "Phamacological Inhibitors of Glycogen Synthase Kinase-3," *Trends in Pharmacol. Sci.* 25(9):471-480 (2004), which is hereby incorporated by reference in its entirety).

Another aspect of the present invention relates to a method of preventing or treating cancer in a subject. This method involves selecting a subject having cancer or at risk of developing cancer and administering a Fbw7 inhibitor to the selected subject under conditions effective to prevent or treat cancer in the subject.

In accordance with this and all other aspects of the present invention, a "subject" or "patient" encompasses any animal, preferably, a mammal. Exemplary mammalian subjects include, without limitation, humans, non-human primates, dogs, cats, rodents (e.g., mouse, rat, guinea pig), horses, cattle and cows, sheep, and pigs. Preferably, the subject is a human.

In one embodiment of this aspect of the present invention, the subject has or is at risk of developing a cancer involving overexpression or aberrant expression of c-Myc protein. In another embodiment of the present invention, the subject has or is at risk of developing leukemia. In particular, the subject has or is at risk of developing chronic myeloid leukemia, acute myeloid leukemia, or B-cell acute lymphoblastic leukemia. In another embodiment of the present invention the subject has or is at risk of developing a solid tumor, such a medullablastoma or glioma.

In another embodiment of the present invention, suitable subjects for treatment in accordance with the methods of the present invention are those subjects having a solid tumor or leukemia that have developed a resistance to conventional cancer therapies. Particularly suitable subjects include those subjects having developed a resistance to tyrosine kinase inhibitor therapy. In another embodiment of the present invention, the subject is one that is at risk for developing relapse disease, in particular relapse chronic myeloid leukemia, acute myeloid leukemia, or B-cell acute lymphoblastic leukemia.

In one embodiment of the present invention, administration of a Fbw7 inhibitor prevents initiation of the cancer or prevents initiation of a particular stage or phase of cancer. For example, Fbw7 treatment can prevent leukemic initiating cell mediated development of lethal CML. In another embodiment of the present invention, administration of a Fbw7 inhibitor prevents the progression of the cancer or leukemia.

Any of the Fbw7 inhibitors described supra can be administered in accordance with this aspect of the invention. In some embodiments of the present invention, it is preferable to target delivery of the Fbw7 inhibitor to only cancer cells to avoid systemic or general inhibition of Fbw7 function. To achieve selective inhibition of Fbw7 in cancer cells only, the inhibitory agent is administered directly to the site of the cancer cells (e.g., direct tumor injection). Alternatively, the Fbw7 inhibitor is housed in a targeted delivery vehicle (suitable delivery vehicles are described infra). In yet another embodiment, selective targeting of the Fbw7 inhibitor is achieved by coupling the inhibitor (or the delivery vehicle containing the inhibitor) to a targeting ligand for directed delivery. Suitable targeting ligands include, without limitation, peptides, aptamers, or antibodies that bind to target cancer cell surface receptor.

A suitable peptide/receptor targeting system, particularly for targeting acute myeloid leukemic cells, involves the transferrin-transferrin receptor system (see e.g., Jin et al., "Targeted Delivery of Antisense Oligodeoxynucleotide by Transferrin Conjugated pH-sensitive Lipopolyplex Nanoparticles: A Novel Oligonucleotide-based Therapeutic Strategy in Acute Myeloid Leukemia," *Mol. Pharm.* 7(1):196-206 (2010), which is hereby incorporated by reference in its entirety).

Fbw7 inhibitor delivery to target cancer cells can also be achieved using antibody delivery systems. In one embodiment of the present invention, a chronic myeloid leukemic cell specific antibody as described by Zhu et al., "Expression of a Humanized Single-Chain Variable Fragment Antibody Targeting Chronic Myeloid Leukemia Cells in *Escherichia coli* and its Characterization," *Int'l, J. Mol. Med.* 29(5):939-45 (2012), which is hereby incorporated by reference in its entirety, is utilized to direct delivery of a Fbw7 inhibitor to chronic myeloid leukemic cells. In another embodiment of the present invention, a monoclonal anti-CD-33 antibody can be utilized to mediated delivery of therapeutic complexes to acute myeloid leukemia cells (Simard et al. "In vivo Evaluation of pH-sensitive Polymer-based Immunoliposomes Targeting the CD33 Antigen," *Mol. Pharm.* 7(4):1098-1107 (2010) and Rothdiener et al., "Targeted Delivery of SiRNA to CD33-positive Tumor Cells with Liposomal Carrier Systems," *J. Control Release* 144(2):251-258 (2010), which are hereby incorporated by reference in their entirety).

In another embodiment of the present invention, a monoclonal anti-CD-19 antibody is coupled to the Fbw7 inhibitor for delivery to leukemic cells, e.g., to acute lymphoblastic leukemic cells. For example, Harata et al., "CD19-targeting Liposomes Containing Imatinib Efficiently Kill Philadelphia Chromosome-positive Acute Lymphoblastic Leukemia Cells," *Blood* 104(5):1442-1449 (2004), which is hereby incorporated by reference in its entirety), describes the use of immunoliposome carrying anti-CD19 antibody (CD19-liposomes) for the delivery of the BCR-ABL tyrosine kinase inhibitor Imatinib to Philadelphia chromosome-positive acute lymphoblastic leukemia at near 100% internalization efficiency. These CD-19 liposome are suitable for targeted delivery of Fbw7 inhibitors in accordance with the methods of the present invention.

Another means of targeting Fbw7 inhibitor delivery to cancer cells, in particular, chronic myeloid leukemia cells, involves the use of lectin conjugated delivery vehicles, such as nanoparticles, containing the Fbw7 inhibitor (Singh et al., "Long Circulating Lectin Conjugated Paclitaxel Loaded Magnetic Nanoparticles: A New Theranostic Avenue for Leukemia Therapy," *PLOS One* 6(11): e26803 (2011), which is hereby incorporated by reference in its entirety).

As an alternative to antibody-based targeting, the Fbw7 inhibitors can be targeted to the appropriate leukemic cells using aptamers. One exemplary aptamer that targets myeloid leukemic cells is KH1C12 [5'-dAdTdCd-CdAdGdAdGdTdGdAdCdGdCdAdGdCdAdTdGdCdCdC dTdAdGdTdTdAdCdTdAdCdTdAdCdT-dCdTdTdTdTdTdAdGdCdAdAdAdCdGdCdCd CdTd-CdGdCdTdTdTdGdGdAdCdAd-CdGdGdTdGdGdGdCdTdTdAdGdT-3'; SEQ ID NO: 5]. This aptamer can be joined to a microRNA or RNAi molecule that inhibits Fbw7 expression or activity, as described. Before joining two functional RNA molecules, it is often beneficial to first predict the secondary structures of the chimeric nucleic acid molecule to ensure that their combination is unlikely to disrupt their secondary structures. Secondary structure predictions can be performed using a variety of software including, without limitation, RNA Structure Program (Dr. David Mathews, University of Rochester) and MFold (Dr. Michael Zuker, The RNA Institute, SUNY at Albany), among others.

In some embodiments of the present invention, it may be desirable to couple the Fbw7 inhibitor to a cell penetrating peptide (CPP) to promote cellular uptake of a Fbw7 inhibitor upon delivery to the target cancer cell. CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, Tat peptide (amino acids 49-57 of HIV Tat protein) and M918, are suitable targeting moieties for use in the present invention and are well known in the art (see Stewart et al., "Cell-Penetrating Peptides as Delivery Vehicles for Biology and Medicine," *Organic Biomolecular Chem* 6:2242-2255 (2008), which is hereby incorporated by reference in its entirety). In particular, a fusion between a Tat-derived peptide (amino acids 49-57) and membrane lytic peptide (LK15), can be utilized to mediate highly efficient delivery of Fbw7 siRNA and shRNA molecules to chronic myeloid leukemic cells (Arthanari et al., "Delivery of Therapeutic shRNA and siRNA by Tat Fusion Peptide Targeting bcr-abl Fusion Gene in Chronic Myeloid Leukemia Cells," *J. Control. Release* 145(3):272-80 (2010), which is hereby incorporated by reference in its entirety). Methods of making CPP are described in U.S. Patent Application Publication No. 20080234183 to Hallbrink et al., which is hereby incorporated by reference in its entirety. The CPP can also be conjugated to a cancer-specific targeting ligand to achieve dual-targeting specificity.

Pharmaceutical compositions containing Fbw7 inhibitors suitable for use in the methods of the present invention can include a pharmaceutically acceptable carrier, one or more active agents, and a suitable delivery vehicle. Suitable delivery vehicles include, but are not limited to viruses, bacteria, biodegradable microspheres, microparticles, nanoparticles, liposomes, collagen minipellets, and cochleates.

In one embodiment of the present invention, the delivery vehicle is a liposome delivery vehicle. Liposomes are vesicles comprised of one or more concentrically ordered lipid bilayers which encapsulate an aqueous phase. A liposome which includes a Fbw7 inhibitor is contacted with the target cancer cell under conditions effective for delivery of the inhibitory agent into the cancer cell. For administration to a primary tumor site, the liposomal vesicles need not be targeted to the cancer cells per se. The liposome delivery system can be made to accumulate at a target organ, tissue, or cell via active targeting (e.g., by incorporating an antibody or other ligand on the surface of the liposomal vehicle). This can be achieved using antibodies or ligands specific for an appropriate cancer cell marker as described supra. See also Simard et al. "In vivo Evaluation of pH-sensitive Polymer-based Immunoliposomes Targeting the CD33 Antigen," *Mol. Pharm.* 7(4):1098-1107 (2010), which is hereby incorporated by reference in its entirety) which describes pH-sensitive immunoliposomes obtained by anchoring a copolymer of dioctadecyl, N-isopropylacrylamide and methacrylic acid in bilayers of PEGylated liposomes and coupling the whole anti-CD33 monoclonal antibody (mAb) or its Fab' fragments to the liposome to deliver a therapeutic payload to human myeloid leukemia cells.

Different types of liposomes can be prepared according to Bangham et al., "Diffusion of Univalent Ions across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

These liposomes can be produced such that they contain, in addition to the Fbw7 inhibitor, other therapeutic agents, such as anti-inflammatory agents, chemotherapeutic agents, or immune-enhancing agents (e.g., IL-2 or interferon alpha), which would also be released at the target site (e.g., Wolff et al., "The Use of Monoclonal AntiThy1-IgG1 for the Targeting of Liposomes to AKR-A Cells in vitro and in vivo," *Biochem. Biophys. Acta* 802:259 (1984), which is hereby incorporated by reference in its entirety).

In another embodiment of the present invention, the delivery vehicle is a nanoparticle. A variety of nanoparticle delivery vehicles are known in the art and are suitable for delivery of a Fbw7 inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include conjugated pH-sensitive lipopolyplex nanoparticles (LPs) as described by Jin et al., "Targeted Delivery of Antisense Oligodeoxynucleotide by Transferrin Conjugated pH-sensitive Lipopolyplex Nanoparticles: A Novel Oligonucleotide-based Therapeutic Strategy in Acute Myeloid Leukemia," *Mol. Pharm.* 7(1):196-206 (2010), which is hereby incorporated by reference in its entirety. The lipopolyplex nanoparticle carrying a therapeutic nucleic acid (e.g. microRNA targeting Fbw7) releases its cargo at acidic endosomal pH to facilitate the cytoplasmic delivery of the therapeutic nucleic acid molecule after endocytosis. Other suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction *In Vivo,*" *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment of the present invention, the delivery vehicle is a viral vector. Viral vectors are particularly suitable for the delivery of inhibitory nucleic acid molecules, such as Fbw7 siRNA or shRNA molecules. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179: 733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Viral vectors are administered to a subject by, for example, intravenous injection, local administration (U.S. Pat. No. 5,328,470 to Nabel et al., which is hereby incorporated by reference in its entirety) or by stereotactic injection (see e.g., Chen et al., "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the gene therapy vector can include the gene therapy vector in an acceptable diluent, or can comprise a slow release matrix in which the gene delivery vehicle is imbedded.

In accordance with this aspect of the present invention, the Fbw7 inhibitor can be administered alone, or alternatively, in combination with another cancer therapy. In one embodiment of the present invention, the Fbw7 inhibitor is administered in combination with a therapeutic used in the treatment of leukemia, in particular chronic myeloid leukemia, such as, for example, a tyrosine kinase inhibitor. Suitable tyrosine kinase inhibitors that can be administered prior to, concurrently with, or subsequent to the Fbw7 inhibitor include, without limitation imatinib mesylate, nilotinib, bosutinib, INNO406, and dasatinib. In another embodiment of the present invention, the Fbw7 inhibitor is administered in combination with omacetaxine mepesuccinate (Omapro), an alkaloid that induces apoptosis by inhibition of protein synthesis. In another embodiment of the present invention, the Fbw7 inhibitor is administered in combination with a farnesyl transferase inhibitor, such as Ionafarnib or tipifarnib. In yet another embodiment of the present invention, the Fbw7 inhibitor is administered in combination with stem cell transplant therapy or surgery (e.g., splenectomy).

In another embodiment of the present invention, the Fbw7 inhibitor is administered in combination with a chemotherapeutic, radiation (e.g., external beam radiation therapy or brachytherapy), an anti-angiogenic therapeutic, or an immune enhancing therapeutic, or any combination thereof.

Suitable chemotherapeutic agents for combination therapies include, without limitation, cytarabine, cyclophosphamide, vincristine, prednisone, daunorubicin, PEG asparaginase, methotrexate, and leucovorin.

Anti-angiogenic therapeutics suitable for use in a combination therapy approach with a Fbw7 inhibitor of the invention include, without limitation, a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art or are under clinical development (see, e.g., Wu et al., "Anti-Angiogenic Therapeutic Drugs for the Treatment of Human Cancer," *J Cancer Molecules* 4(2):37-45 (2008), which is hereby incorporated by reference in its entirety). These angiogenic inhibitors include, without limitation, Gefitinib (an ErbB inhibitor), Lapatinib (a dual ErbB1/ErbB2 inhibitor), Erlotinib, Canertinib (a pan-ErbB inhibitor), Vatalanib (VEGF receptor inhibitor), Sunitinib (multi-targeted inhibitor of VEGFR, PDGFR Kit, Flt3, Tet and CSF1R inhibitor), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Another aspect of the present invention is directed to a method of preventing or treating chronic myeloid leukemia in a subject. This method involves selecting a subject having chronic myeloid leukemia or at risk of developing chronic myeloid leukemia and administering a c-Myc inhibitor or GSK3 inhibitor to the selected subject under conditions effective to prevent or treat chronic myeloid leukemia in the subject.

Suitable c-Myc and GSK3 inhibitors for use in accordance with this aspect of the present invention are described supra.

Suitable methods for targeting delivery of c-Myc and GSK3 inhibitors to the desired cancer cell populations and delivery vehicles are also described supra.

In one embodiment of this aspect of the present invention, the subject having chronic myeloid leukemia is in chronic phase. In another embodiment of the present invention, the subject having chronic myeloid leukemia is in late chronic/accelerated phase myeloid leukemia. In yet another embodiment of the present invention, the subject having chronic myeloid leukemia is in blast crisis phase of the disease.

In another embodiment of the present invention, the selected subject has refractory chronic myeloid leukemia. Accordingly, the selected subject may be resistant to first generation tyrosine kinase inhibitor treatment (e.g., treatment with imatinib mesylate), and/or resistant to second generation tyrosine kinase inhibitor treatment (e.g., treatment with dasatinib or nilotinib). In yet another embodiment of the present invention, the subject has relapse chronic myeloid leukemia.

In accordance with this aspect of the present invention, the c-Myc and GSK3 inhibitors can be administered alone, or alternatively, in combination with another cancer therapy, such as a chronic myeloid leukemia treatment (e.g., tyrosine kinase inhibitor), chemotherapeutic, radiation (e.g., external beam radiation therapy or brachytherapy), an anti-angiogenic therapeutic, or an immune enhancing therapeutic, or any combination thereof as described supra.

In practicing the methods of the various aspects of the present invention, the administering step is preferably carried out to achieve cancer cell specific inhibition of Fbw7, c-Myc, and/or GSK3 and such administration can be carried out systemically or via direct or local administration, i.e., to a tumor site. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, stenting, ear/eye drops, or portal vein administration to relevant tissues, or any other local administration technique, method or procedure, as is generally known in the art.

The therapeutic agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the Fbw7, c-Myc, or GSK3 inhibitors of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

Compositions containing Fbw7, c-Myc, or GSK3 inhibitors may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the compositions of the present invention, for the treatment of cancer vary depending upon many different factors, including type and stage of cancer, means of administration, target site, physiological state of the patient, other medications or therapies administered, and physical state of the patient relative to other medical complications. Treatment dosages need to be titrated to optimize safety and efficacy using methods known to those of skill in the art.

EXAMPLES

The following examples are provided to illustrate embodiments of the present invention but they are by no means intended to limit its scope.

Materials and Methods for Examples 1-10

Animals

Fbw7$^{flox}$ mice were previously published (Thompson et al., "Control of Hematopoietic Stem Cell Quiescence by the E3 Ubiquitin Ligase Fbw7," *J. Exp. Med.* 205:1395-1408 (2008), which is hereby incorporated by reference in its entirety). Myc$^{flox}$ mice were a kind gift from F. Alt (de Alboran et al., "Analysis of c-Myc Function in Normal Cells Via Conditional Gene-Targeted Mutation," *Immunity* 14:45-55 (2001), which is hereby incorporated by reference in its entirety), and Myc$^{eGFP}$ mice were a kind gift from Dr. Barry Sleckman (Huang et al., "Dynamic Regulation of c-Myc Proto-Oncogene Expression During Lymphocyte Development Revealed by a GFP-c-Myc Knock-In Mouse," *Eur. J. Immunol.* 38:342-349 (2008), which is hereby incorporated by reference in its entirety). IFNa-inducible Mx1-cre, p53 germline knockout, and C57B16 recipient mice were purchased from Jackson Laboratories. The Vav-Cre transgenic line was provided by the Graf laboratory (Stadtfeld & Graf, "Assessing the Role of Hematopoietic Plasticity for Endothelial and Hepatocyte Development by Non-Invasive Lineage Tracing," *Development* 132:203-213 (2005), which is hereby incorporated by reference in its entirety). All mice were housed in a pathogen-free animal facility at the NYU School of Medicine. All animal procedures were carried out in compliance with Institutional Animal Care and Use Committee of the NYU School of Medicine.

FACS Analysis:

All antibodies used for FACS analysis were procured from e-Bioscience. Specifically, the antibodies used were as follows: c-kit (2B8), Sca-1 (D7), Mac-1 (M1/70), Gr-1 (RB6-8C5), NK1.1 (PK136), TER-119, CD3 (145-2C11), CD19 (1D3), IL7R (RAM34), CD4 (RM4-5), CD8 (53-6.7), CD271 (NGFR) (ME20.4). BM lineage antibody cocktail includes the following: Mac-1, Gr-1, NK1.1, TER-119, CD4, CD8, IL7R and CD19. Apoptosis was detected using Annexiv-V PE-conjugated detection kit (BD Pharmingen) along with 7-AAD following manufacturers protocol.

Generation and Analysis of Disease Mice for In Vivo Studies:

Genotyping of mouse strains was preformed as previously described (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety), and primers are listed in Table 1. Mice, 4-6 weeks old, were sacrificed and the bone marrow was flushed from femurs and tibias. Single cell suspensions were prepared, and red blood cells were lysed NH$_4$Cl buffer for 3 minutes on ice. Subsequently, Lin$^-$ cells were obtained using the mouse hematopoietic progenitor enrichment kit (Stem Cell Technologies) per manufacturer's protocol and stained with a lineage cocktail, cKit, and Sca-1 antibodies. LSK cells were sort purified and cultured overnight at 37° C. in 5% CO$_2$ in Opti-MEM medium (Gibco) supplemented with 10% FBS (Sigma Aldrich), 1% Penn/Strep (Gibco), 100 ng/mL of mouse recombinant SCF (Peprotech) and 20 ng/mL of mouse recombinant TPO (Peprotech) in 96 well U-bottom plates (cell density was ~20,000 cells/well). Twelve hours post cell sort, cells were infected with Bcr-Abl-NGFR or Bcr-Abl-GFP retrovirus (Wertheim et al., "BCR-ABL-Induced Adhesion Defects are Tyrosine Kinase-Independent," *Blood* 99:4122-4130 (2002), which is hereby incorporated by reference in its entirety) and spun at 2500 rpm for 90 minutes at 30° C. The plates were incubated at 37° C. in 5% CO$_2$ for four hours and then the media was carefully aspirated and replaced with fresh medium. The infection procedure was repeated for a second time the next day and the cells were allowed to rest for 24 hours following infection. Finally, the infection efficiency (~20-40%) was determined by flow cytometry and Bcr-Abl-NGFR$^+$ or Bcr-Abl-GFP$^+$ LSK cells were transplanted (cells were normalized to ~20,000-40,000 Lineage$^-$Bcr-Abl-NGFR$^+$ LSKs for each genotype) into congenic lethally irradiated (2×550 rads) recipient mice with 2–5×10$^5$ support bone marrow cells. Deletion of Fbw7, p53, and c-Myc was initiated on day 7 post transplantation 3 injections every other day with poly(I:C) (Amsersham) at a concentration of 10 ug/g of body weight. Disease development was assessed by the presence of Bcr-Abl$^+$ cells in the peripheral blood by flow cytometry. Mice were sacrificed and analyzed upon exhibiting physical signs of disease, such as hunched posture, rough coat, and limited movement.

TABLE 1

Genotyping Primers

| | |
|---|---|
| FBW7-R recombined allele | ggcttagcatatcagctatgg (SEQ ID NO: 6) |
| FBW7 R | atagtaatcctcctgccttggc (SEQ ID NO: 7) |
| FBW7 F | attgatacaaactggagacgagg (SEQ ID NO: 8) |
| MxCre F | gcctacaatatggatttccca (SEQ ID NO: 9) |
| MxCre R | cttgcgaacctcatcactc (SEQ ID NO: 10) |
| C-MYC R | ttttctttccgattgctgac (SEQ ID NO: 11) |
| C-MYC F | taagaagttgctattttggc (SEQ ID NO: 12) |
| C-MYC R recombined allele | tcgcgccoctgaattgctagga (SEQ ID NO: 13) |
| C-MYC F | ccgaccgggtccgagtccctatt (SEQ ID NO: 14) |
| p53-WT | acagcgtggtggtaccttat (SEQ ID NO: 15) |
| p53-GT-Common | tatactcagagccggcct (SEQ ID NO: 16) |
| p53-GT-MUT | ctatcaggacatagcgttgg (SEQ ID NO: 17) |

For secondary transplantation experiments, mice were sacrificed approximately 20 days after the initial transplantation and whole spleen (normalized for ~10,000-20,000 Bcr-Abl$^+$ LSKs for each genotype) was transplanted into lethally irradiated (2×550 rads) secondary recipient mice.

For B-ALL experiments, total BM was isolated and transduced with Bcr-Abl-GFP retrovirus followed by culture overnight at 37° C. in 5% CO$_2$ in Opti-MEM medium supplemented with 10% FBS, 1% Penn/Strep, and 10 ng/ml mouse recombinant IL-7 (Peprotech) at a density of 5×10$^6$ cells per well in a 6-well plate (Corning). The following day, transduction efficiency was determined by flow cytometry, and 2×10$^6$ cells were transplanted into congenic lethally irradiated (2×550 rads) recipient mice. Twelve day post-transplant peripheral samples were obtained and monitored for Bcr-Abl-GFP$^+$ B220$^+$ cells. Day 13 post transplantation mice underwent 3 injections every other day with poly(I:C) (Amsersham) at a concentration of 20 ug/g of body weight. Peripheral blood was once again monitored for Bcr-Abl-GFP$^+$ B220$^+$ cells at day 21 post-transplantation, and recipients were followed for disease development.

All mice were analyzed using FACS analysis and hematoxylin and eosin staining of formalin-fixed paraffin embedded tissues (i.e. liver and lung). Peripheral blood was smeared on a slide and subsequently stained using the Giemsa-Wright staining method. Deletion of genotypes was measured by genomic PCR as previously described (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety).

In Vitro Colony Forming Unit Assays:

For the in vitro CFU experiments, mice received 5 intraperitoneal (IP) injections of poly(I:C) at a dose of 20 ug/g, and LSK cells were purified 10 days post poly(I:C). LSK cells were purified and infected with Bcr-Abl-NGFR or Bcr-Abl-GFP retrovirus as described above. Bcr-Abl$^+$ lineage negative cells were sorted 72 hours after the first infection and 1000 cells were seeded into cytokine-supplemented methylcellulose medium (MethoCult 3434, Stem Cell Technologies). Colonies were counted 7 days after they were seeded and 4000 cells were re-plated and colonies were counted after another 7 days (14 days total). For human CFU assay, cells were collected after 7 days of culture, and 1×10$^3$ CD34$^+$Lin$^-$ cells were transferred to Methocult medium (MethoCult GF H4435, StemCell Technologies). The number of colonies was counted 1 week after plating.

Immunoblot Analysis:

Immunoblotting was carried out as previously described (Thompson et al., "Control of Hematopoietic Stem Cell Quiescence by the E3 Ubiquitin Ligase Fbw7," *J. Exp. Med.* 205:1395-1408 (2008), which is hereby incorporated by reference in its entirety). LSKs or ckit$^+$ BM cells were lysed with RIPA lysis buffer (50 mM TrisHCl, 150 mM NaCl, 0.1% SDS, 0.5% NaDeoxycholate, 1% NP40) and cells were incubated on ice for 20 minutes and cellular debris were pelleted by ultra-centrifugation. Total cell lysates were separated by SDS-PAGE on a 10% Tris-HCl gel and were transferred to nitrocellulose membranes. Membranes were probed with anti-c-Myc (9402, Cell Signaling), anti-phospho-c-Myc (Cell Signaling), anti-cleaved Notch 1 (2421, Cell Signaling), anti-Bcr (3902, Cell Signaling), and anti-actin (Clone C4, Milipore) antibodies. Blots incubated with secondary horseradish peroxidase (HRP) conjugated anti-mouse IgG or anti-rabbit antibodies (Amersham, GE Healthcare Biosciences Piscataway, N.J.) in TBS-T according the manufacturer's protocol. Bands were visualized using chemiluminescence (GE Healthcare).

siRNA-Mediated Depletion:

Viable bone marrow mononuclear cells from two treatment-naïve patients in the chronic phase of CML were obtained from AllCells. To examine the role of FBW7 in the maintenance of LICs for human CML, bone marrow mononuclear cells were transfected with 300 nM FBW7 siRNAs (Stealth Select RNAi siRNA, Invitrogen) by electroporation with the use of an Amaxa Nucleofector II device (Lonza) according to the manufacture's instructions. The transfected cells were then stained with antibodies to human CD34 (8G12), CD3 (SK7), CD16 (3G8), CD19 (SJ25C1), CD20 (L27), CD14 (MφP9), and CD56 (NCAM16.2) (BD Biosciences). CD3, CD16, CD19, CD20, CD14, and CD56 were used as lineage markers. CD34$^+$Lin$^-$ cells were purified by FACS and cocultured with OP-9 cells for 7 days. For assays of apoptosis, cells were collected after 7 days of culture, stained for cell surface markers, further incubated for 15 min with annexin V (BD Biosciences) and then analyzed by flow cytometry.

Quantitative Real-Time PCR:

Total RNA was harvested from cells using the Qiagen RNeasy Kit (Qiagen, Germany). RNA was quantified by absorbance at A260 nm and 2 μg of total RNA was used for cDNA synthesis using Superscript III first strand synthesis kit (Invitrogen). Q-RT-PCR was carried out using SYBR green universal mix PCR reaction buffer (Roche) using a Roche Lightcycler 480 II. All signals were normalized to levels of Gapdh. qRT-PCR primers are included Table 2.

TABLE 2 qRT-PCR Primers

| species | gene | sequence |
|---------|------|----------|
| mouse | Puma F | gcggcggagacaagaaga (SEQ ID NO: 18) |
| mouse | Puma R | agtcccatgaagagattgtacatgac (SEQ ID NO: 19) |
| mouse | p21F | ttccgcacaggagcaaagt (SEQ ID NO: 20) |
| mouse | p21R | cggcgcaactgctcact (SEQ ID NO: 21) |
| mouse | Bax F | tggagctgcagaggatgattg (SEQ ID NO: 22) |
| mouse | Bax R | agctgccacccggaaga (SEQ ID NO: 23) |
| mouse | Fbw7 F | gtgatagagccccagttcca (SEQ ID NO: 24) |
| mouse | Fbw7 R | cctcagccaaaattctccag (SEQ ID NO: 25) |
| mouse | c-Myc F | cttctctccttcctcggactc (SEQ ID NO: 26) |
| mouse | c-Myc R | ggagatgagcccgactccgacctc (SEQ ID NO: 27) |
| human | FBW7 F | gtgatagaaccccagtttca (SEQ ID NO: 28) |
| human | FBW7 R | cttcagccaaaattctccag (SEQ ID NO: 29) |
| human | c-MYC F | gctgcttagacgctggattt (SEQ ID NO: 30) |
| human | Myc R | cgaggtcatagttcctgttgg (SEQ ID NO: 31) |
| human | GAPDH-F | cttttgcgtcgccagccgag (SEQ ID NO: 32) |
| human | GAPDH-R | ccaggcgcccaatacgacca (SEQ ID NO: 33) |

Isolation of Human CD34+ and Lentivirus Transduction:

Bone marrow mononuclear cells from patients in different phases of CML were kindly provided by Dr. Abdel-Wahab (Leukemia Service, Memorial Sloan Kettering Cancer Center). UCB or patient BM CD34$^+$ cells were isolated using CD34$^+$ selection kit following manufacturer's instructions (Stem Cell Technologies). Cells were cultured in Stemspan (Stem Cell Technologies), supplemented with 50 ng/ml SCF, 50 ng/ml Flt3L, and 100 ng/ml Tpo for 24 hours followed by two spinoculation with virus supernatant (2,500 RPM, 30°, 90 minutes). Twenty-four hours post infection, cells were selected with 2 μg/ml puromycin for 48 hrs. KU812 cell line was cultured in RPMI+10% FCS, and was infected in similar manner, pLKO shRNA plasmids against FBW7 were purchased from Sigma.

CD34$^+$CD38$^+$ and CD34$^+$CD38$^{low/-}$ cells were purified by FACS using CD34 PE-conjugated and CD38 FITC conjugated antibodies (BD Pharmingen).

Statistical Analysis:

All the statistical analyses were performed using un-paired two-tailed Student's t-test assuming experimental samples of equal variance, unless otherwise specified.

Example 1

Fbw7 Deletion is Able to Suppress Initiation of Bcr-Abl-Induced CML

To address the role of Fbw7 in the self-renewal and differentiation of leukemia-initiating cells a well-established animal model of chronic phase Bcr-Abl-induced CML was utilized (Daley et al., "Blast Crisis in a Murine Model of Chronic Myelogenous Leukemia," *Proc. Nat'l. Acad. Sci. U.S.A.* 88:11335-11338 (1991); Neering et al., "Leukemia Stem Cells in a Genetically Defined Murine Model of Blast-Crisis CML," *Blood* 110:2578-2585 (2007); Pear et al., "Efficient and Rapid Induction of a Chronic Myelogenous Leukemia-Like Myeloproliferative Disease in Mice Receiving P210 bcr/abl-Transduced Bone Marrow," *Blood* 92:3780-3792 (1998), which are hereby incorporated by reference in their entirety). In this model, Bcr-Abl expressing retroviruses are used to infect highly-purified hematopoietic stem and progenitor cells, Lineage$^{neg}$c-Kit$^+$Sca1$^+$ (LSK). Transduced LSKs are then transplanted into lethally irradiated congenic hosts, which develop a CML-like disease that is characterized by the accumulation of Bcr-Abl$^+$ CD11b$^+$ Gr1$^+$ cells in the peripheral blood (PB), splenomegaly and tissue infiltration. The pathology of the disease replicates chronic phase CML due to <2% of the mononuclear population within the peripheral blood have blast morphology whereas the majority of the mononuclear population displays morphology consistent with mature myeloid cells. Mice succumb to disease starting at approximately 25-30 days post cell transplantation (FIG. 1D).

To initially test the role of Fbw7 function in CML in vitro, a conditional Fbw7 allele (Vav1cre$^+$Fbw7$^{f/f}$) (Stadtfeld & Graf, "Assessing the Role of Hematopoietic Plasticity for Endothelial and Hepatocyte Development by Non-Invasive Lineage Tracing," *Development* 132:203-213 (2005); Thompson et al., "The SCFFBW7 Ubiquitin Ligase Complex as a Tumor Suppressor in T Cell Leukemia," *J. Exp. Med.* 204:1825-1835 (2007), which are hereby incorporated by reference in their entirety) was used that specifically targets deletion in hematopoietic cells, starting from the HSC subset during development, and purified LSK cells from 2 to 4 week old mice (before any significant alterations of the LSK compartment are evident) (Matsuoka et al., "Fbxw7 Acts as a Critical Fail-Safe Against Premature Loss of Hematopoietic Stem Cells and Development of T-ALL," *Genes Dev.* 22(8): 986-91 (2008); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety). Fbw7$^{-/-}$ and Fbw7$^{w/w}$ LSK cells were infected with Bcr-Abl retroviruses, sorted by flow cytometry for Bcr-Abl$^+$, and plated on colony-forming unit (CFU) assays. Control (Bcr-Abl$^+$Fbw7$^{+/+}$) LSK cells generated colonies at the first plating and were able to serially replate for several passages demonstrating extensive proliferation potential (FIG. 1A). Interestingly, Bcr-Abl$^+$Fbw7$^{-/-}$ LSK cells generated only a few small colonies at the first plating and were unable to re-plate, suggesting direct effects of Fbw7 deletion on survival of the cells. This was an unexpected finding, as "wild-type" (Bcr-Abl$^{neg}$) Fbw7$^{-/-}$ LSK cells are able to efficiently generate colonies at the first plating, and their colony forming ability is only progressively lost (FIG. 2) (Reavie et al., "Regulation of Hematopoietic Stem Cell Differentiation by a Single Ubiquitin Ligase-Substrate Complex," *Nat. Immunol.* 11:207-215 (2010); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety), suggesting distinct responses to Fbw7 deletion between physiological and leukemic LSK cells. To address Fbw7 function in CML in vivo, LSKs were infected with Bcr-Abl-expressing retroviruses and transplanted into lethally irradiated recipient mice. Control Bcr-Abl expressing cells (purified from littermate Vav1cre$^+$Fbw7$^{w/w}$ mice) were able to initiate disease and progress to lethal CML (FIGS. 1B-1D). On the other hand, Bcr-Abl-expressing Fbw7$^{-/-}$ LSK cells were unable to initiate disease and recipient animals did not developed CML (FIGS. 1B-1D). These effects on the initiation of CML were not a consequence of Fbw7 deletion on HSC homing and engraftment suggesting direct role on maintenance of Bcr-Abl$^+$ cells (FIG. 2). These data suggest that Fbw7 deletion inhibits Bcr-Abl induced CML induction due to direct effects on Bcr-Abl$^+$ LSK cell maintenance.

Example 2

Fbw7 Deletion is Able to Suppress Bcr-Abl-Induced Disease Progression

Figures 3A, 3B:
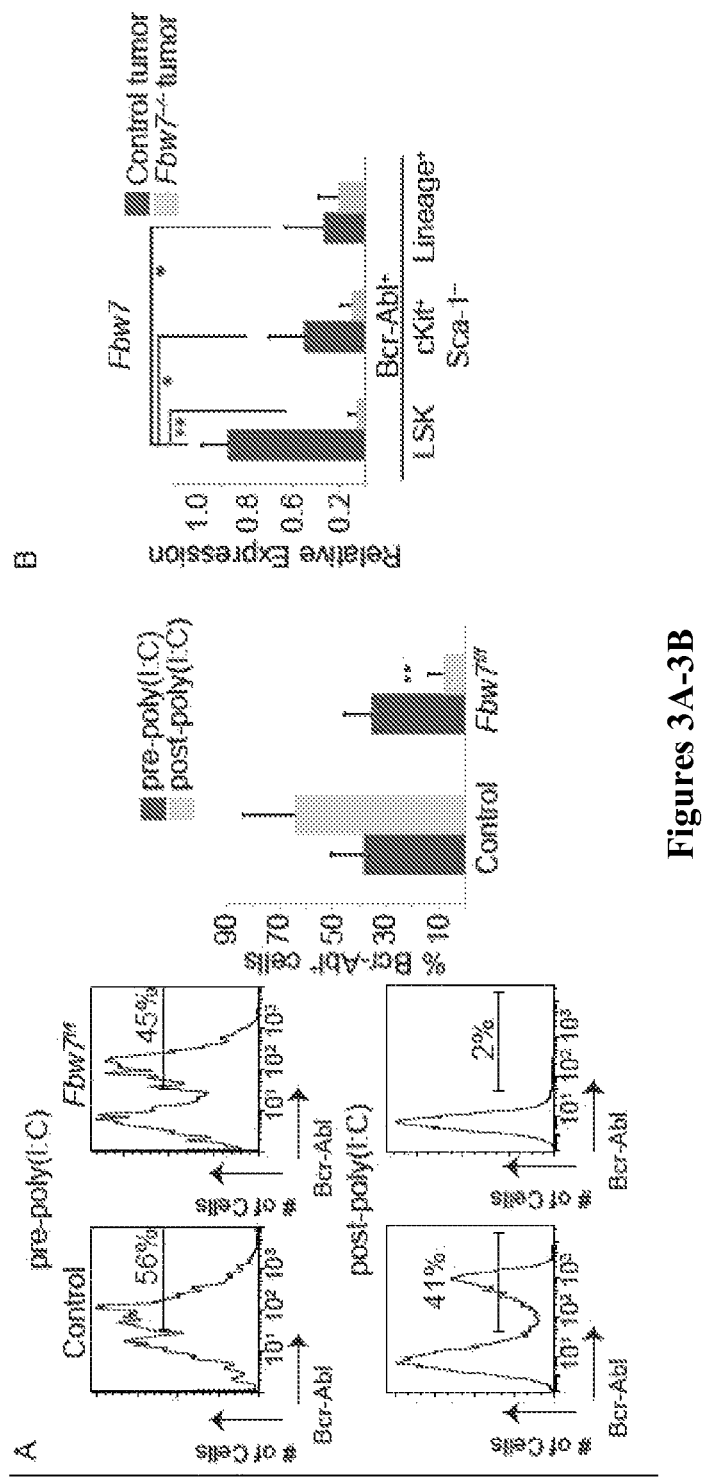
FIGS. 3A-3F demonstrate that Fbw7 is essential for progression of established CML in vivo.
Figures 3C, 3D:
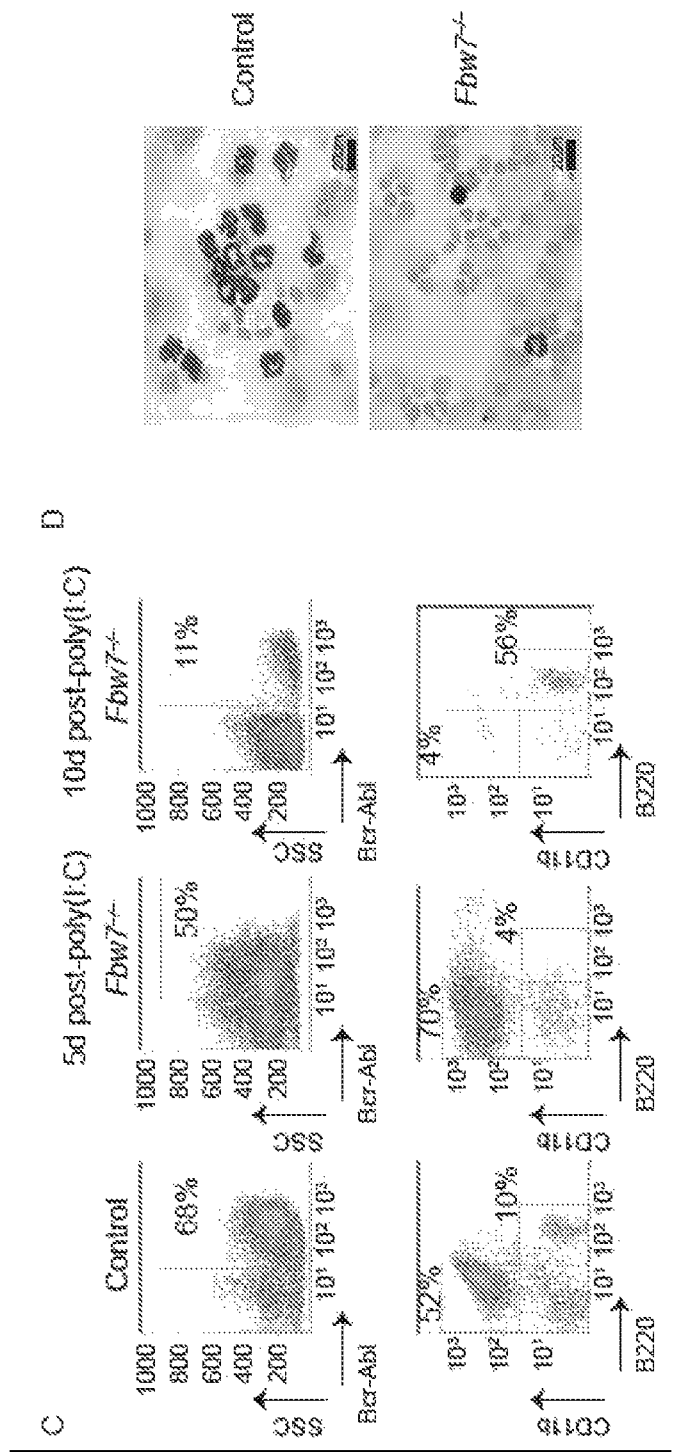
Figures 3E, 3F:
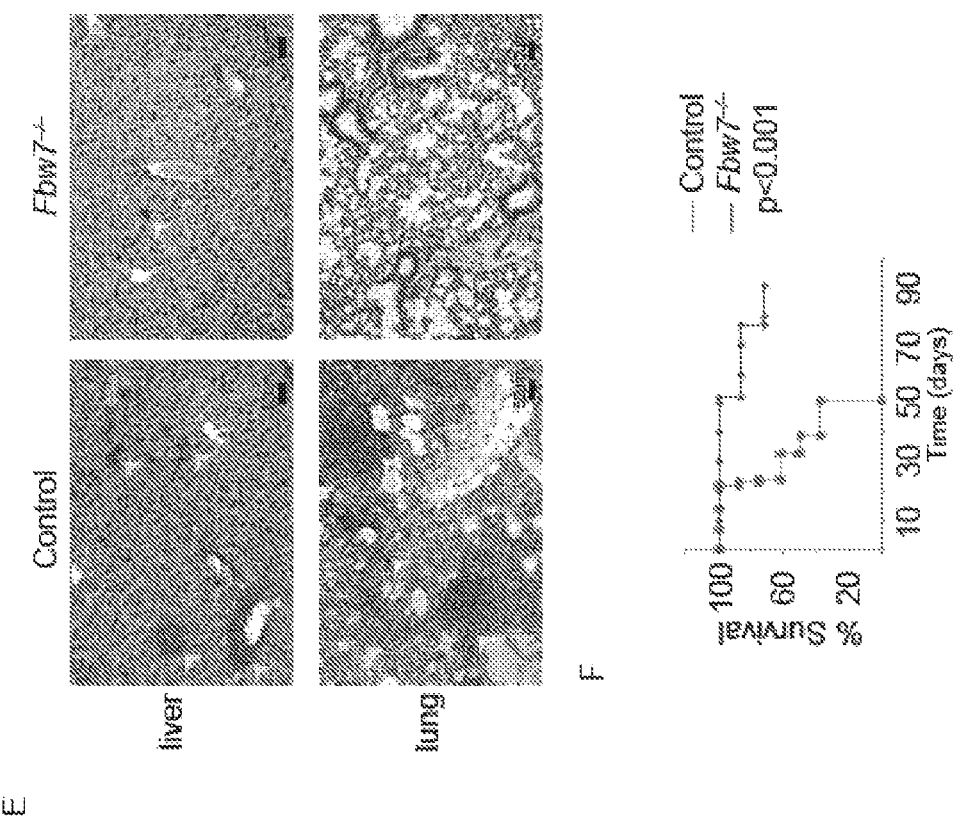

These experiments address effects of Fbw7 on transformation but do not study its role during progression of CML in vivo. To experimentally address this question Fbw7$^{f/f}$ mice were crossed to Mx1cre mice, which Cre-recombinase is active as early as the HSC stage upon administration of polyI-polyC (Mx1cre$^+$Fbw7$^{f/f}$). This allows for gene deletion after the onset of the disease. In these experiments CML was established by Bcr-Abl-expressing Mx1cre$^+$Fbw7$^{f/f}$ and littermate control Bcr-Abl-expressing LSK cells. Disease onset was verified by flow cytometry 7 days post-transplantation (FIG. 3A). Fbw7 gene deletion was achieved by three polyI-polyC injections and confirmed by quantitative reverse transcriptase PCR (qRT-PCR) analysis (FIG. 3B). Notably, tumor LSKs expressed the highest levels of Fbw7 when compared to more differentiated subsets (FIG. 3B). Similar to previous observations, control recipients developed CML as characterized by the accumulation of Bcr-Abl$^+$CD11b$^+$Gr1$^+$ cells in the bone marrow (FIG. 3C), peripheral blood (FIGS. 3A and 3D) and peripheral organs such as the spleen, liver and lung (FIG. 3E). In contrast, polyI-polyC-mediated deletion of Fbw7 led to a rapid reversal of CML progression (as judged by both Bcr-Abl$^+$ and CD11b$^+$ absolute cell numbers, FIGS. 3A and 3C) resulting in almost no infiltration of secondary tissues by leukemic cells (FIG. 3E). More importantly, while all control mice succumbed to the disease by day 50 post-transplantation, recipient animals transplanted with Bcr-Abl$^+$ Mx1cre$^+$Fbw7$^{f/f}$ cells and injected with polyI-polyC did not succumb to the disease (FIG. 3F). These studies demonstrated that Fbw7 deletion is also able to suppress further development of CML and lead to disease remission, suggesting effects on putative leukemia-initiating cells.

Example 3

Fbw7 Deficient Bcr-Abl Cells have No Leukemia-Initiating Activity In Vivo

Figures 4A, 4B, 4C:
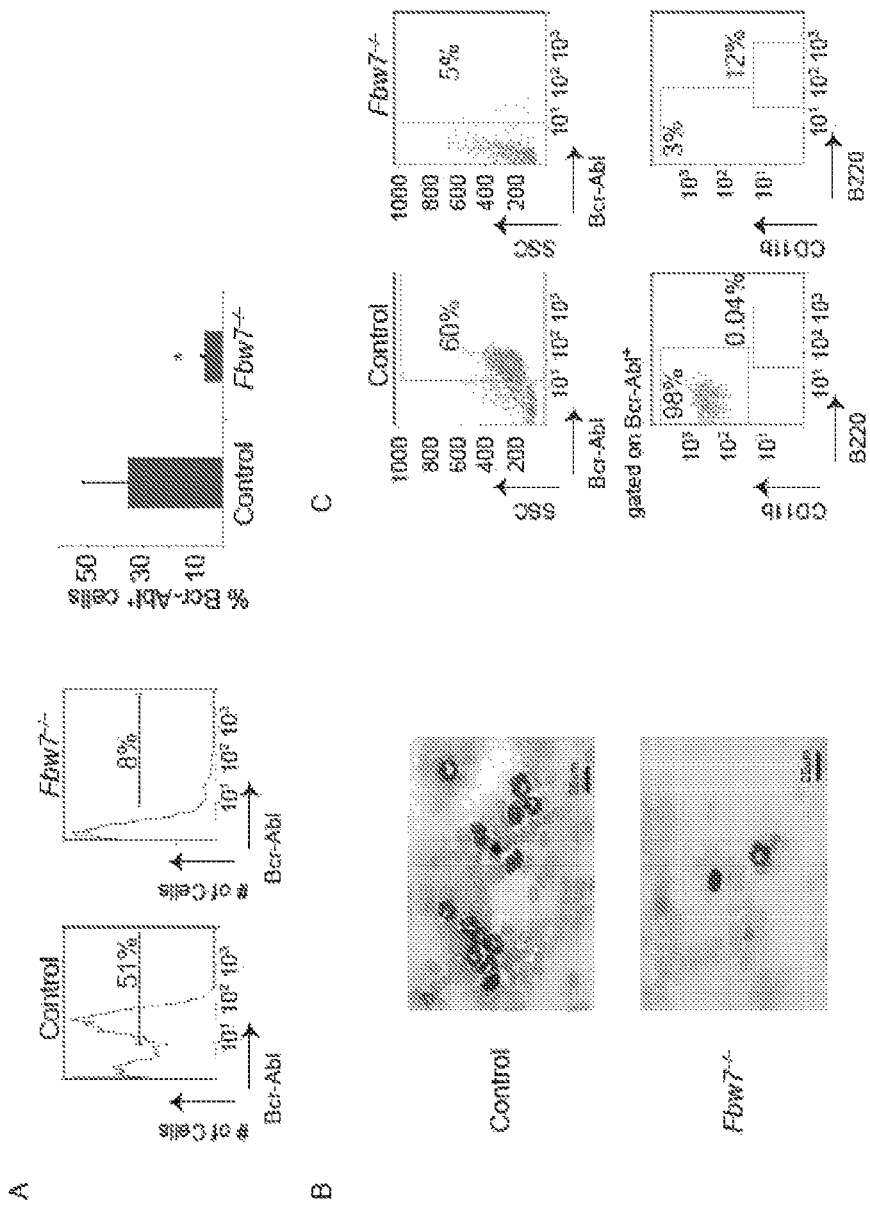
FIGS. 4A-4E show that Fbw7 deficiency affects leukemia-initiating cell activity in a mouse model of CML.
Figures 4D, 4E:
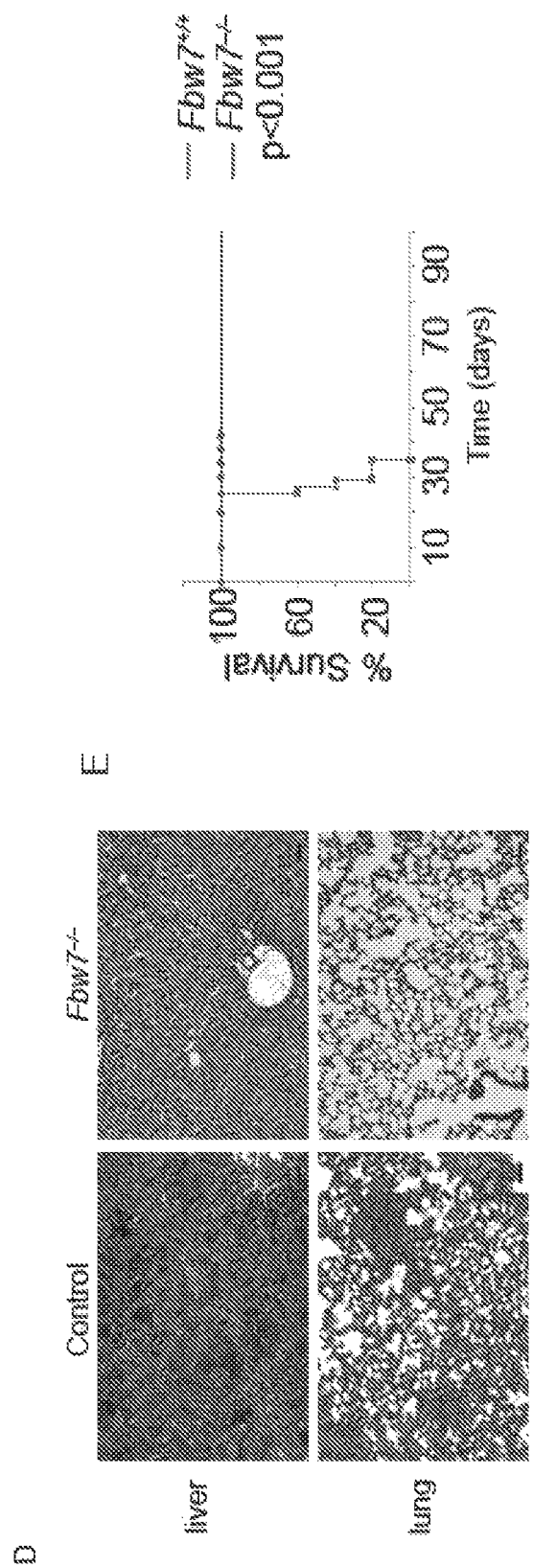

To directly test the self-renewal capacity of the LIC fraction, secondary transplantation experiments were performed using whole spleen cells isolated approximately 10 days after polyI-polyC-treatment from Mx1cre$^+$Fbw7$^{-/-}$ and littermate controls, respectively. To ensure that identical numbers of Bcr-Abl$^+$ LSKs were transplanted in both cohorts, the total number of spleen cells was normalized based on the frequency of Bcr-Abl+ LSK cells determined by FACS analysis. Disease onset and progression were subsequently studied. In agreement with the previous findings, recipients of Fbw7$^{-/-}$ tumor cells did not develop CML (FIG. 4A). In contrast, control Bcr-Abl+ cells harbored LIC activity when transplanted into secondary recipients and transferred disease exhibiting the same hallmarks as the primary CML (FIGS. 4B-4D) and rapidly (≤30 days) led to lethal CML (FIG. 4E). No effects on the viability of hosts that received Fbw7$^{-/-}$ Bcr-Abl+cells were noted (FIG. 4E). These results indicate that Fbw7 deletion in established CML specifically inhibits LIC activity.

Example 4

Fbw7 Deletion Affects Survival of CML Initiating Cell Populations

Figures 2A, 2B, 2C, 2D, 2E, 2F:
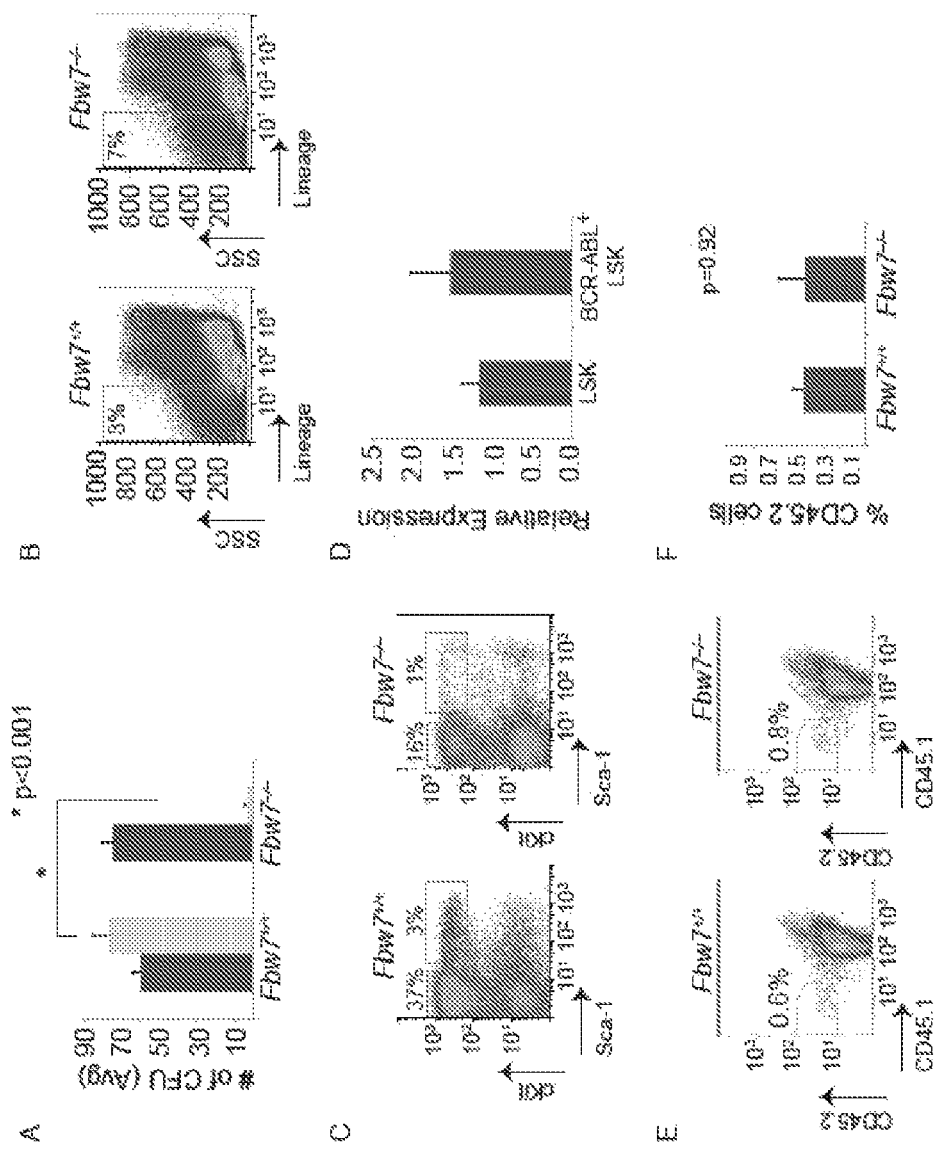
FIGS. 2A-2F show that Fbw7 deletion results in progressive loss of stem and progenitor cell re-populating capacity.
Figures 5A, 5B:
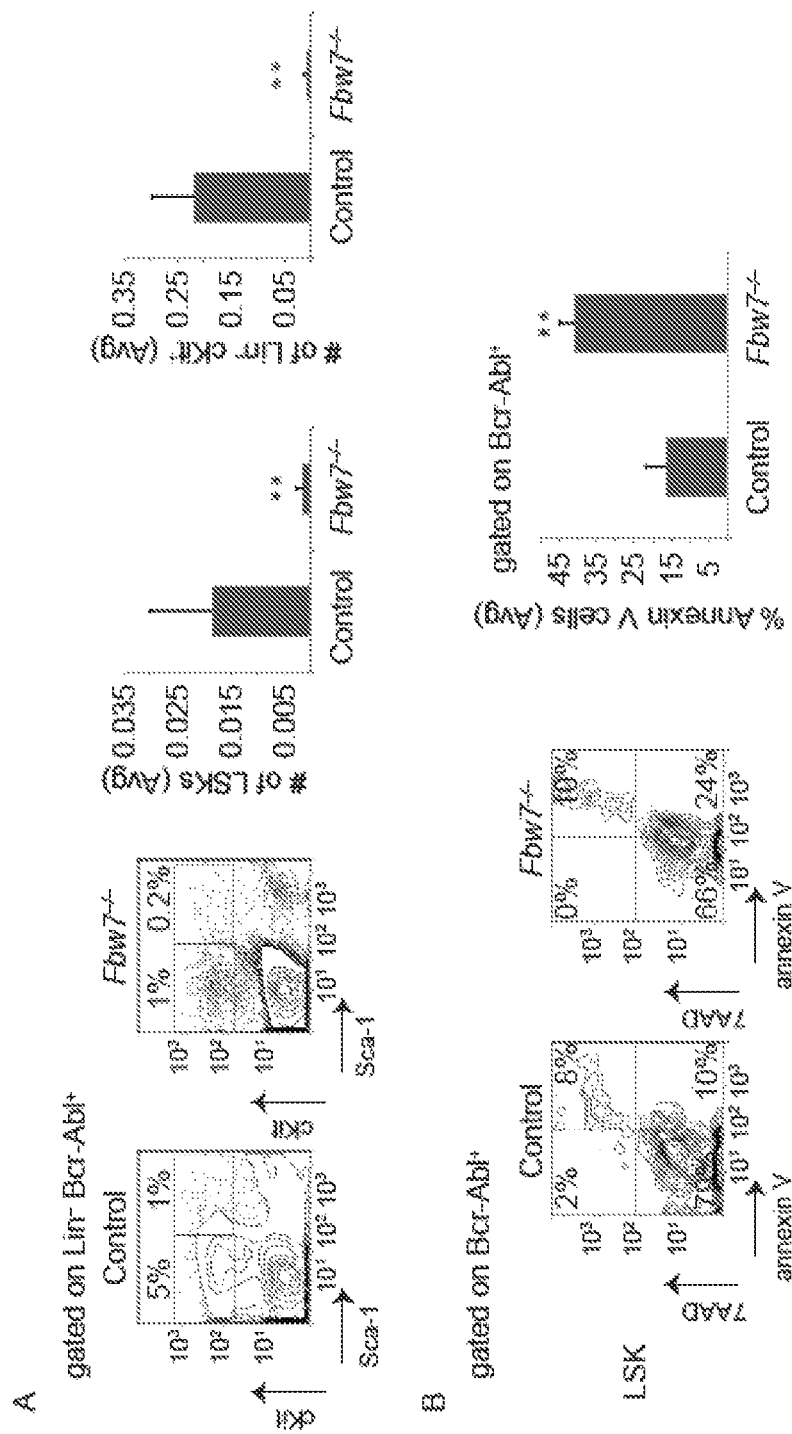
FIGS. 5A-5C demonstrate that Fbw7 deletion affects CML-initiating cell survival through the activation of the p53 pathway.
Figure 5C:
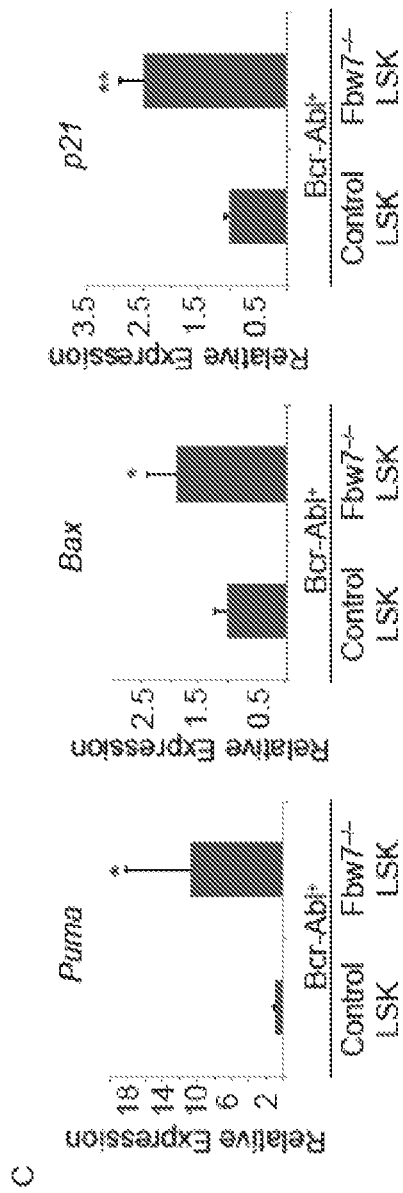

It was previously shown that the LIC activity in Bcr-Abl-induced CML is confined to the Lineage$^{neg}$c-Kit+ and specifically the LSK subset of the Bcr-Abl-expressing tumor (Neering et al., "Leukemia Stem Cells in a Genetically Defined Murine Model of Blast-Crisis CML," *Blood* 110: 2578-2585 (2007), which is hereby incorporated by reference in its entirety). To directly study putative effects of Fbw7 deletion in these subsets both their relative representation and their absolute numbers in response to Fbw7 deletion (using the inducible Mx1cre+Fbw7$^{f/f}$ in vivo model) were studied. PolyI-polyC-mediated Fbw7 deletion in established CML led to the rapid and significant loss of Lineage$^{neg}$c-Kit+ and more specifically the LSK populations (FIG. 5A). Interestingly, at the same time points, more differentiated Bcr-Abl-expressing tumor cells were detected, albeit at a lower frequency than control cohorts, suggesting that deletion of Fbw7 specifically targets immature, putative LIC, leukemia subsets (FIG. 3C). The acute loss of Bcr-Abl+ LSK cells following Fbw7 deletion was significantly more rapid than what has been reported for physiological (wild-type, Bcr-Abl$^{neg}$) LSK cells, which takes 3-4 months (Matsuoka et al., "Fbxw7 Acts as a Critical Fail-Safe Against Premature Loss of Hematopoietic Stem Cells and Development of T-ALL," *Genes Dev.* 22(8):986-91 (2008); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety). Quantitative RT-PCR studies showed that CML LSK cells express slightly higher levels of Fbw7 mRNA than WT LSK but this difference is not statistically significant (FIG. 2D). Moreover, Fbw7 function is mainly regulated post-translationally, at the level of substrate abundance and phosphorylation (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety). To identify a putative mechanism to explain the impact of Fbw7 deletion on the Bcr-Abl+ LSK population, a subset that harbors all the LIC activity in this disease model (Neering et al., "Leukemia Stem Cells in a Genetically Defined Murine Model of Blast-Crisis CML," *Blood* 110: 2578-2585 (2007), which is hereby incorporated by reference in its entirety), apoptosis and cell death was evaluated using Annexin-V and 7AAD (FIG. 5B). As shown in FIG. 5B, Fbw7 deletion led to a rapid and significant increase (5-8 fold) in the fraction of the Bcr-Abl+ LSK cells undergoing apoptosis suggesting direct induction of cell death in this progenitor subset. p53 target genes associated with cell survival were evaluated by qRT-PCR. Puma, Bax, p21 and Noxa were up-regulated in Fbw7$^{-/-}$ tumor LSKs, suggesting that p53 pathway activation mediates the induced death of Fbw7 deficient Bcr-Abl+ LSK cells (FIG. 5C). These studies provide the biological mechanism explaining the loss of Bcr-Abl+ LICs and the suppression of disease progression in response to Fbw7 deletion.

Example 5 c-Myc is the Key Substrate Targeted by Fbw7 in CML-Initiating Cell Populations

Figures 6A, 6B, 6C, 6D:
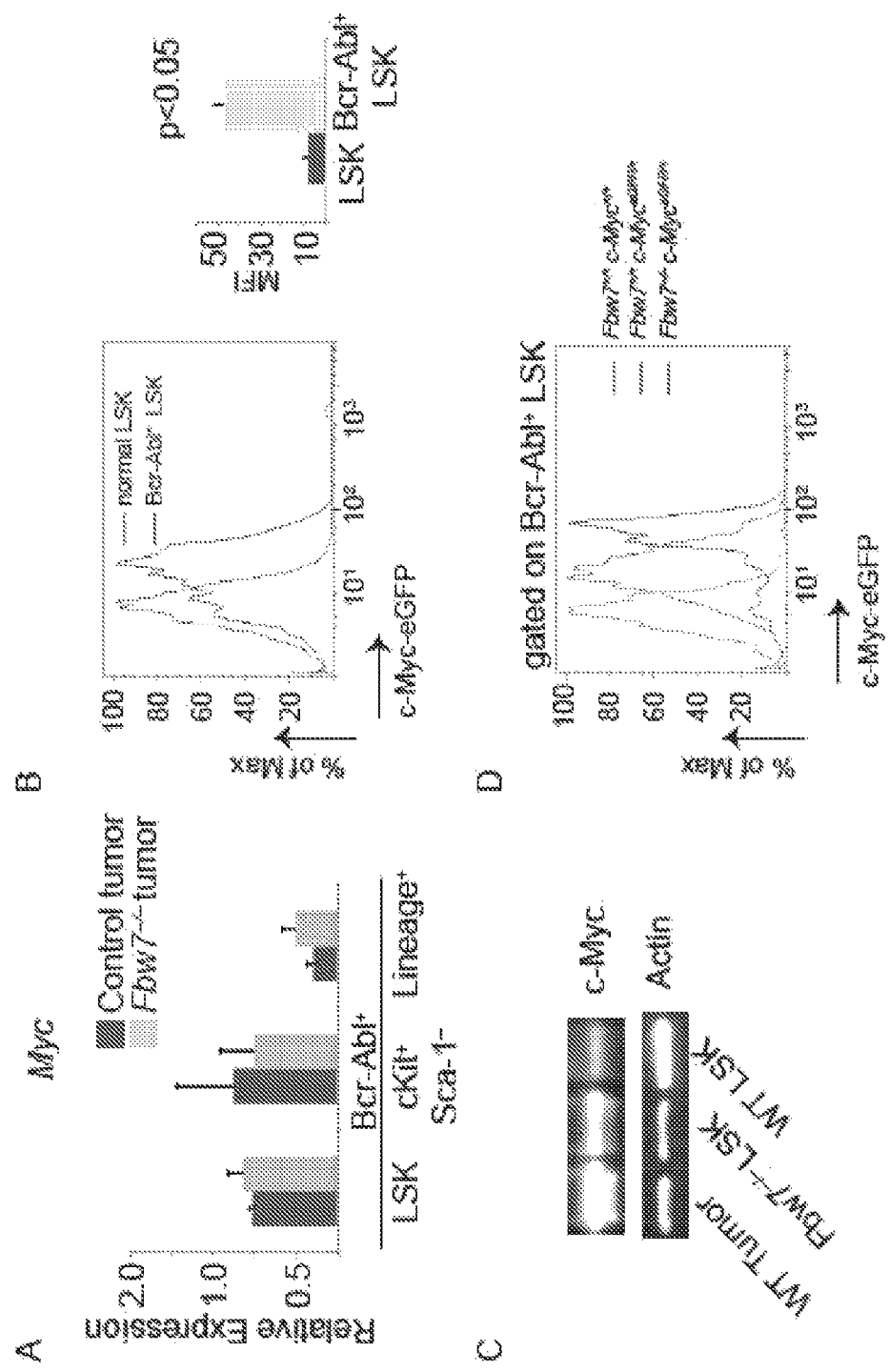
FIGS. 6A-6I demonstrate that a decrease in c-Myc protein levels and inhibition of p53 activation are able to rescue CML-initiating activity in vitro and in vivo.

It has previously been shown that c-Myc is an Fbw7 substrate during early hematopoiesis (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety) and that CML is dependent on Bcr-Abl induction of c-Myc (Nakamura et al., "Down-Regulation of Thanatos-Associated Protein 11 by BCR-ABL Promotes CML Cell Proliferation Through c-Myc Expression," *Int. J. Cancer* 130 (5):1046-59 (2012); Xie et al., "Involvement of Jak2 Tyrosine Phosphorylation in Bcr-Abl Transformation," *Oncogene* 20:6188-6195 (2001), which are hereby incorporated by reference in their entirety). Therefore, it was a possibility that "unphysiologically" high levels of the oncogenic c-Myc protein could cause the cell death observed upon loss of Fbw7 expression in established CML. This was most likely through activation of the p53 pathway since p53 target genes were upregulated in Fbw7$^{-/-}$ Bcr-Abl+ LSKs (FIG. 5C). Since differential effects of Fbw7 deletion on wild-type and Bcr-Abl+ LSK function in vitro have been shown (FIGS. 1 and 2), levels of c-Myc protein in these two subsets were directly compared by taking advantage of a targeted c-Myc allele that expresses a c-Myc-eGFP fusion protein (c-Myc$^{eGFP}$). This is a functional protein fusion and a faithful indicator of endogenous c-Myc protein levels (Huang et al., "Dynamic Regulation of c-Myc Proto-Oncogene Expression During Lymphocyte Development Revealed by a GFP-c-Myc Knock-In Mouse," *Eur. J. Immunol.* 38:342-349 (2008); Reavie et al., "Regulation of Hematopoietic Stem Cell Differentiation by a Single Ubiquitin Ligase-Substrate Complex," *Nat. Immunol.* 11:207-215 (2010), which are hereby incorporated by reference in their entirety). This animal model provides the ability to visualize in vivo the relative levels of c-Myc protein abundance in CML and study protein expression changes in response to the deletion of Fbw7 (FIGS. 6B and 6D). Despite the fact that c-Myc mRNA levels were unchanged between control and Fbw7 deficient Bcr-Abl+ LSKs (FIG. 6A), using this allele (Mx1cre+Fbw7$^{f/f}$c-Myc$^{eGFP/wt}$), Bcr-Abl+ LSK cells expressed significantly higher c-Myc protein levels than wild-type (non-leukemic) LSK cells purified from littermate mice (FIG. 6B). This data was further corroborated by western blot protein quantification (FIG. 6C). Notably, c-Myc protein levels were higher in leukemic LSKs (WT Tumor) when compared to both WT LSK and Fbw7$^{-/-}$ LSKs, potentially explaining the different physiological responses observed between non-leukemic and leukemic LSKs in response to Fbw7 deletion (FIG. 6C). In Bcr-Abl+ LSK cells, loss of Fbw7 expression further induced the levels of c-Myc protein beyond that observed in WT leukemic LSK cells (FIG. 6D). These data suggest that slight changes in c-Myc protein abundance could result in distinct phenotypic responses.

Figures 7A, 7B, 7C, 7D:
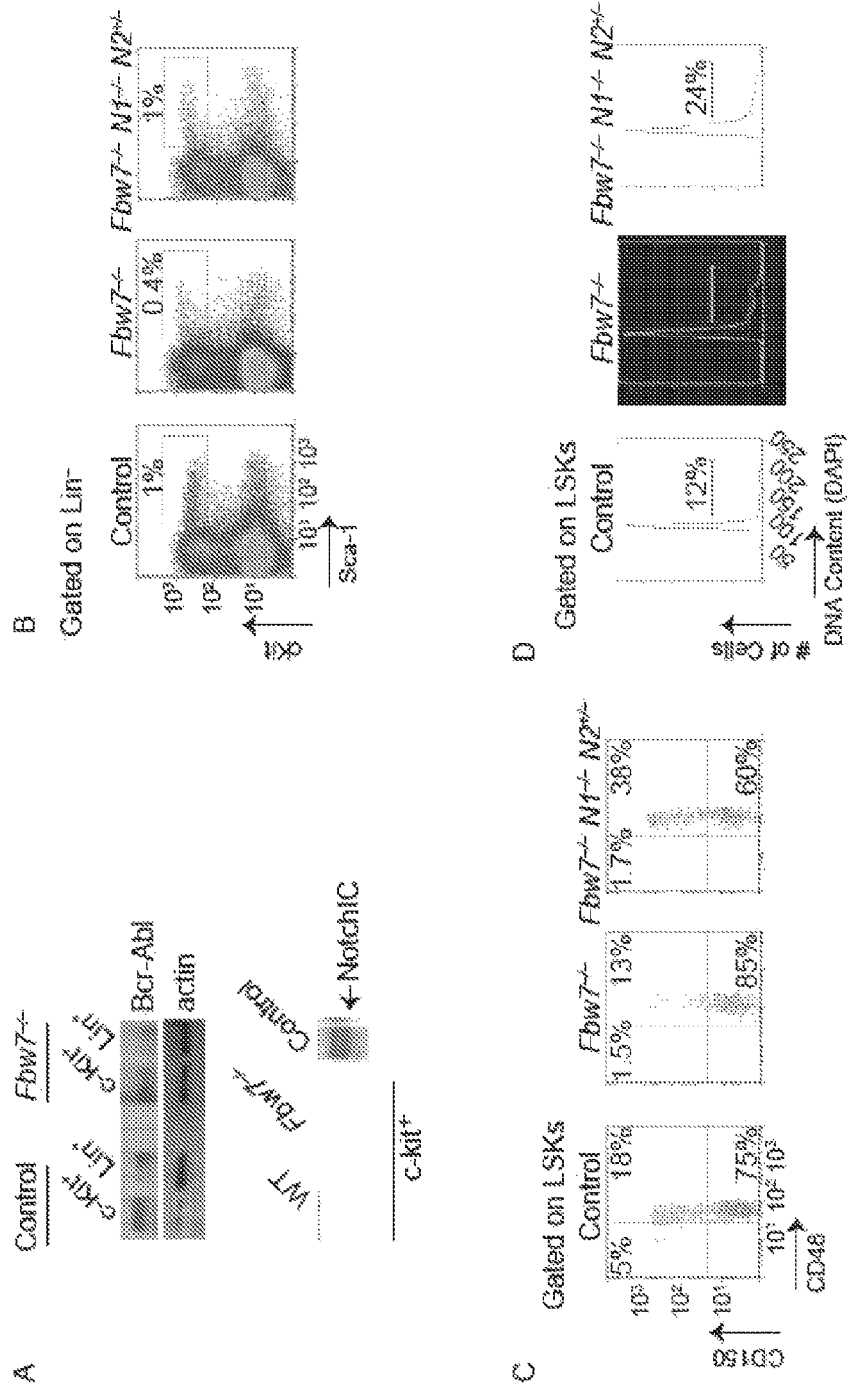
FIGS. 7A-7E show that Notch stability does not contribute to Fbw7 induced HSC defects.
Figure 7E:
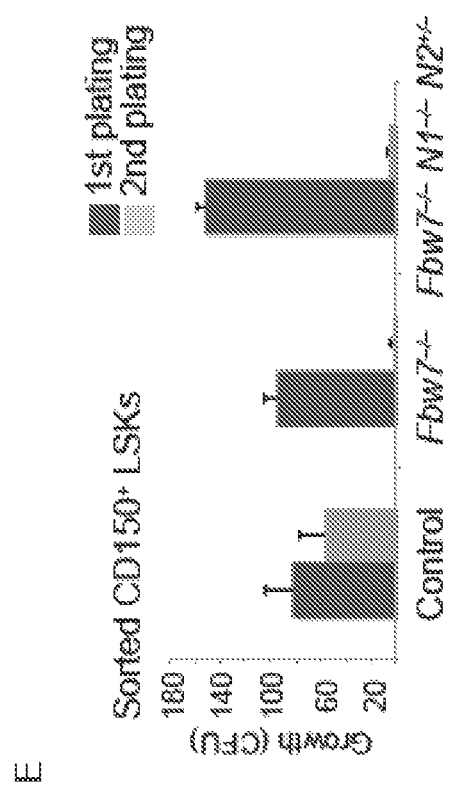

Additional Fbw7 substrates, particularly Notch has been previously implicated in CML progression (Ito et al., "Regulation of Myeloid Leukaemia by the Cell-Fate Determinant Musashi," *Nature* 466:765-768 (2010), which is hereby incorporated by reference in its entirety), could likely influence the observed LIC defects upon Fbw7 deletion in Bcr-Abl$^+$ LSKs. To address this question, the expression level of cleaved Notch1 in WT and Fbw7$^{-/-}$ Bcr-Abl$^+$ c-kit$^+$ cells was evaluated. Expression of Notch1 was not detected in either population (FIG. 7A). Of note, Notch1 and Notch2 do not appear to be Fbw7 substrates in wild-type HSCs as generation of triple knockout mice (MxCre$^+$Fbw7$^{f/f}$/Notch1$^{f/f}$/Notch2$^{f/f}$) could not rescue the HSC defects observed in Fbw7$^{-/-}$LSKs (non-leukemic) (FIG. 7B). More specifically, the frequency (total cell number) of CD150$^+$ CD48$^-$ LSKs and aberrant cell cycle status were unaffected by reducing Notch levels in Fbw7 deficient mice (FIGS. 7B-7D) (Thompson et al., "Control of Hematopoietic Stem Cell Quiescence by the E3 Ubiquitin Ligase Fbw7," *J. Exp. Med.* 205:1395-1408 (2008), which is hereby incorporated by reference in its entirety). These in vivo studies have defined for the first time the effects of Fbw7 on leukemia initiating cell populations. They have also demonstrated that c-Myc (and not Notch1/2) is the major Fbw7 substrate in CML.

Example 6

Figures 6E, 6F, 6G, 6H, 6I:
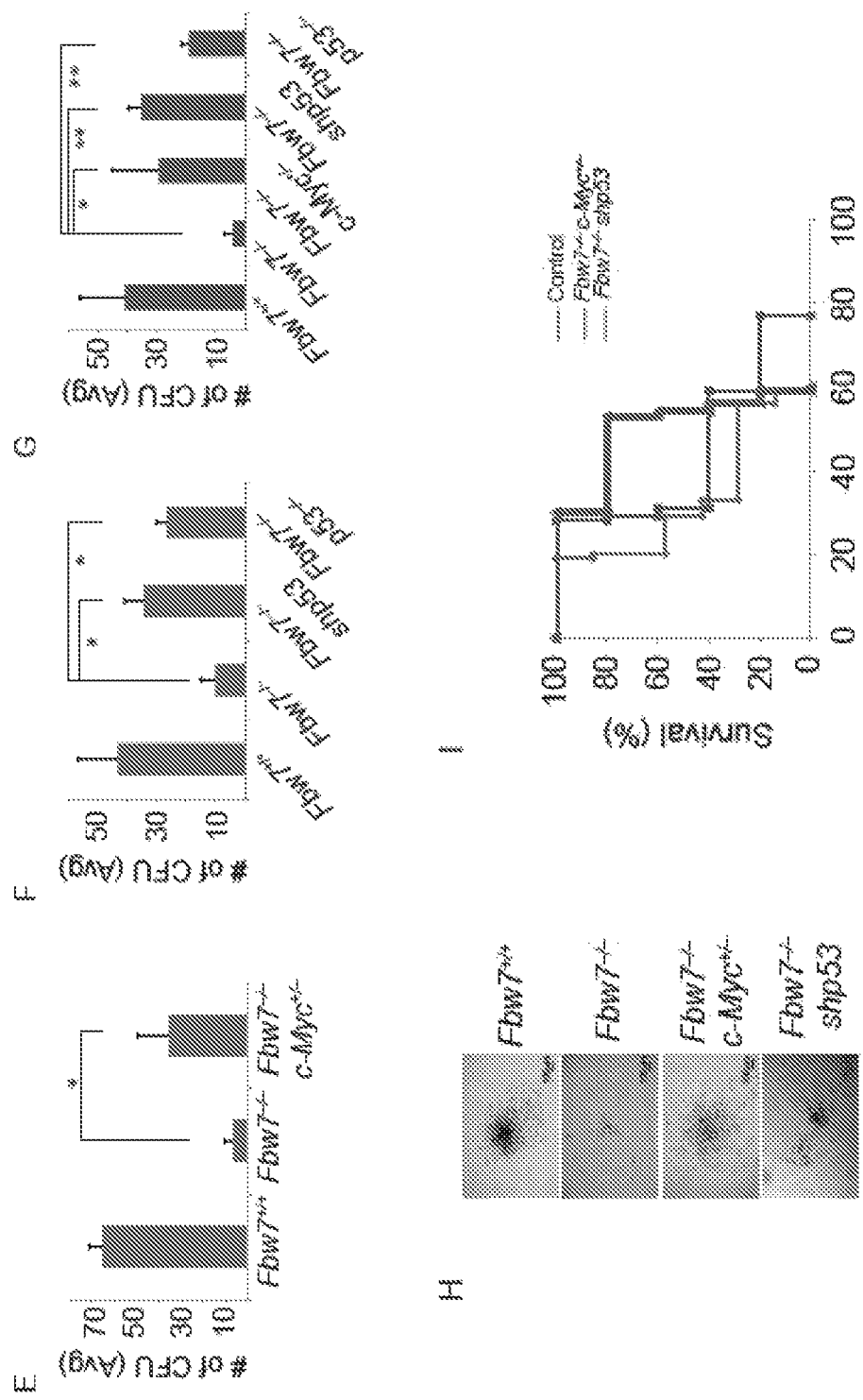
Figures 8A, 8B, 8C:
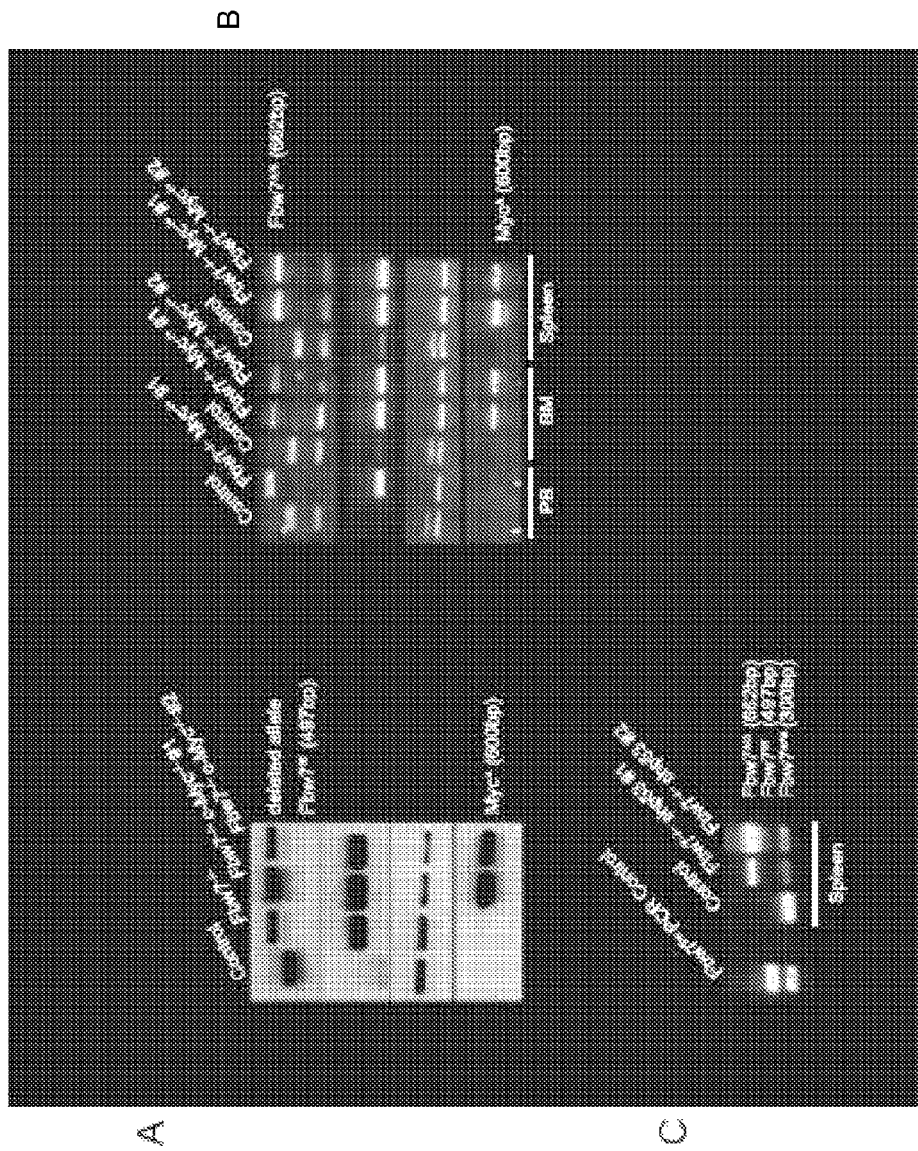
FIGS. 8A-8C depict the results of PCR used to confirm deletion of conditional alleles. Representative genotyping PCR for mouse models used throughout the manuscript.

Decrease of c-Myc Protein Levels and p53 Silencing Rescues Fbw7$^{-/-}$ LIC Function To directly address the mechanisms of action of Fbw7 in CML-initiating cells a genetic rescue Fbw7 deletion effects on the survival of the Bcr-Abl$^+$ LSK population was attempted. Mx1cre$^+$Fbw7$^{f/f}$c-Myc$^{f/w}$ mice were generated, p53 expression was silenced in Mx1cre$^+$Fbw7$^{f/f}$ cells using a p53-specific shRNA (Brie et al., "Functional Identification of Tumor-Suppressor Genes Through an In Vivo RNA Interference Screen in a Mouse Lymphoma Model," *Cancer Cell* 16:324-335 (2009), which is hereby incorporated by reference in its entirety) and Mx1cre$^+$Fbw7$^{f/f}$p53$^{-/-}$ double knock out (DKO) mice were generated (referred herein as p53$^{-/-}$). It was hypothesized that a decrease in c-Myc protein levels and the inhibition of p53 response could rescue the ability of Fbw7$^{-/-}$Bcr-Abl$^+$LSK cells to maintain CML disease progression in vivo and serially replate in vitro. As shown in FIGS. 6E-6I both genetic modifications led to a significant rescue of the ability of the Fbw7 deficient LSK cells to generate colonies in vitro and to induce disease in-vivo. The Fbw7$^{-/-}$c-Myc$^{-/w}$, Fbw7$^{-/-}$ shp53 and Fbw7$^{-/-}$ p53$^{-/-}$ DKO colonies were almost indistinguishable in numbers from colonies generated by wild-type cells, and no significant qualitative (i.e. cell lineage biases) differences were noted (FIG. 6E-6H). Fbw7$^{-/-}$c-Myc$^{-/w}$ and Fbw7$^{-/-}$p53$^{-/-}$ colonies can re-plate over several passages in a fashion identical to wild-type counterparts (FIG. 6G). Since in-vitro assays do not directly assess the self-renewal ability of LICs, transduced LSKs from Fbw7$^{-/-}$c-Myc$^{-/w}$ and Fbw7$^{-/-}$ shp53 were transplanted into lethally irradiated congenic recipients. Importantly, mice receiving Bcr-Abl$^+$ LSKs from Fbw7$^{-/-}$ c-Myc$^{-/w}$ developed a CML-like disease with similar kinetics to mice injected with Bcr-Abl$^+$ control cells restoring Fbw7$^{-/-}$ LIC self-renewal capacity (FIG. 6I). However, as previously shown by Lowe and colleagues loss of p53 in CML leads to disease progression, and Bcr-Abl$^+$ shp53$^+$ LSKs from Fbw7$^{-/-}$ progressed to an accelerated phase based on pathology and 5% blasts in the periphery (Wendel et al., "Loss of p53 Impedes the Antileukemic Response to BCR-ABL Inhibition," *Proc. Nat'l. Acad. Sci. U.S.A.* 103:7444-7449 (2006), which is hereby incorporated by reference in its entirety). Deletion of all alleles was determined for all experiments by genomic PCR (FIG. 8). These experiments demonstrate that c-Myc over-expression and p53-mediated toxicity are responsible for the apoptotic phenotype of the Fbw7 deficient LIC.

Example 7

In Vivo Visualization of c-Myc Protein Expression in CML

Figures 9A, 9B:
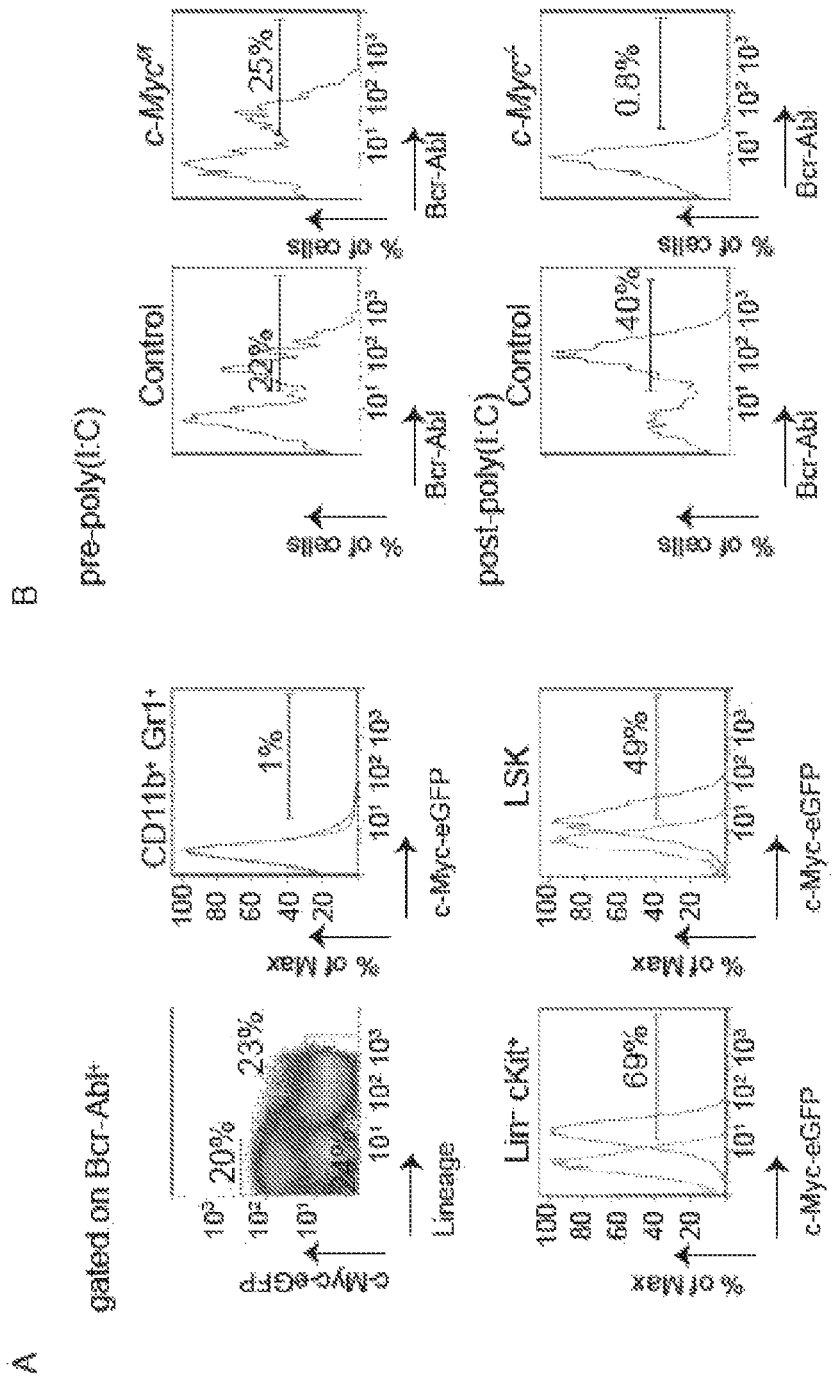
FIGS. 9A-9D show that CML-initiating cell activity and disease progression depends on c-Myc expression and activity.
Figures 10A, 10B, 10C:
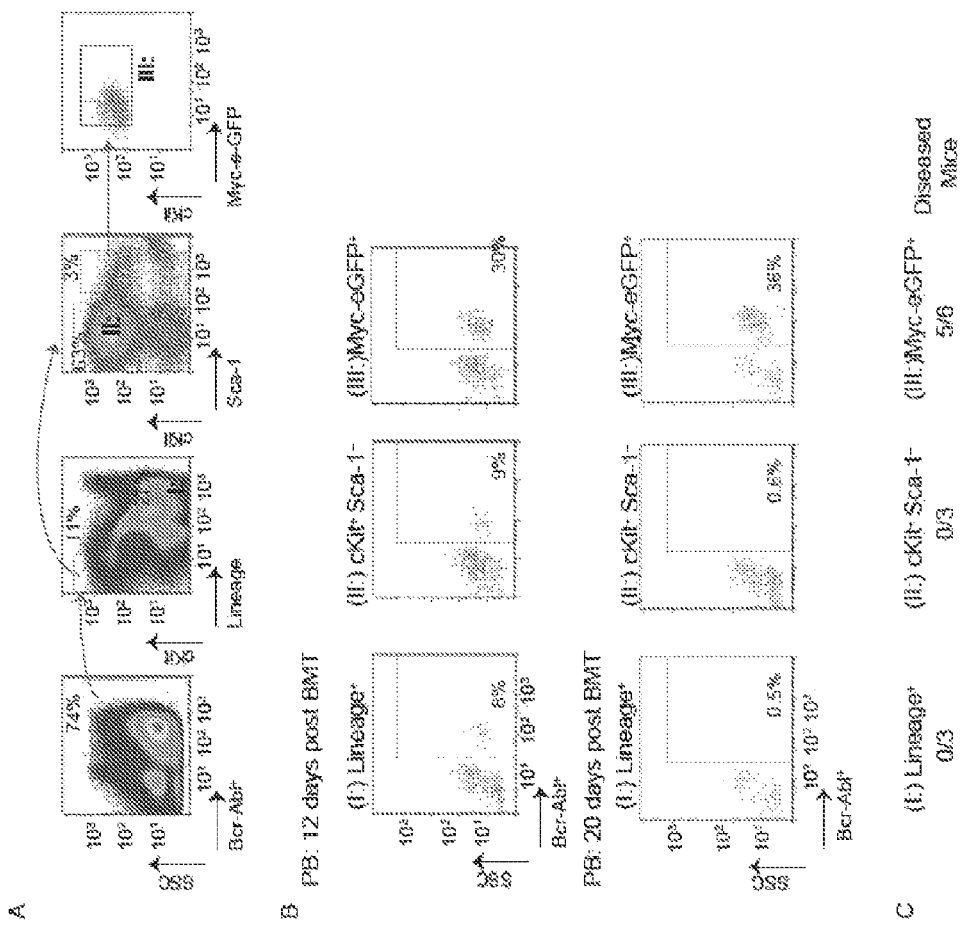
FIGS. 10A-10C show that leukemia initiating cell potential is specific to c-Myc$^+$ LSK.

These studies suggested that CML-initiating cells express c-Myc protein. Although it was previously shown that Bcr-Abl is able to induce c-Myc expression (Nakamura et al., "Down-Regulation of Thanatos-Associated Protein 11 by BCR-ABL Promotes CML Cell Proliferation Through c-Myc Expression," *Int. J. Cancer* 130(5):1046-59 (2012); Xie et al., "Jak2 is Involved in c-Myc Induction by Bcr-Abl," *Oncogene* 21:7137-7146 (2002), which are hereby incorporated by reference in their entirety) it is unclear whether c-Myc function is essential for the initiation or/and the progression of the disease. To address this question the c-Myc$^{eGFP}$ genetic model was utilized and c-Myc expression in established CML was visualized. As shown in FIG. 9A, only a minority of CML (Bcr-Abl$^+$) cells express detectable levels of c-Myc protein. All c-Myc expression is confined within the Lineage$^{neg}$ fraction and comprises approximately 10-20% of the bulk of the tumor, where c-Myc protein expression was detected in Lin$^{neg}$ cKit$^+$ and LSK cells. In contrast, mature CD11b$^+$ Gr1$^+$ cells (the majority of the tumor) are c-Myc/GFP$^{neg}$ (FIG. 9A). To test whether there is a correlation between leukemia-initiating activity and c-Myc protein expression different tumor subsets were purified and identical cell numbers were transplanted into secondary recipients. Neither the Lin$^{pos}$ c-Myc/eGFP$^{neg}$ nor the Lin$^{neg}$ c-Myc/eGFP$^{neg}$ fractions were able to transfer disease (FIG. 10). On the other hand, all leukemia-initiating activity was confined to the c-Myc$^{eGFP}$ leukemic cell fraction (FIGS. 10B and 10C). However, flow cytometry-based separation of Bcr-Abl$^+$c-Kit$^+$Sca1$^-$ and Bcr-Abl$^+$c-Kit$^+$Sca1$^+$ (LSK) fractions, coupled to subsequent transplantation experiments demonstrated that only the LSK fraction could transfer disease in secondary hosts (FIGS. 10B and 10C). Further separation of c-Myc$^{eGFP-LOW/INT}$ and c-Myc$^{eGFP-HIGH}$ LSK cells failed to show that the leukemia-initiating activity lies within a specific subset, in agreement with expression studies that showed that the vast majority of LSK cells express c-Myc mRNA and protein (FIGS. 9A and 12). This finding contrasts with c-Myc protein expression and function in normal LSK cells, where the population clearly contains a c-Myc$^{neg}$ fraction that maintains quiescence and HSC activity and a c-Myc$^{pos}$ fraction containing MPP (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety). Indeed, c-Myc$^{eGFP}$-expressing normal LSK cells have no stem cell activity. These are the first in vivo c-Myc visualization studies in any type of leukemia and suggest that although LIC activity lies within the c-Myc-expressing fraction, c-Myc protein expression is not sufficient to guarantee leukemia-initiating properties.

Example 8

Bcr-Abl-Induced CML is Addicted to c-Myc Expression and Function

Figures 9C, 9D:
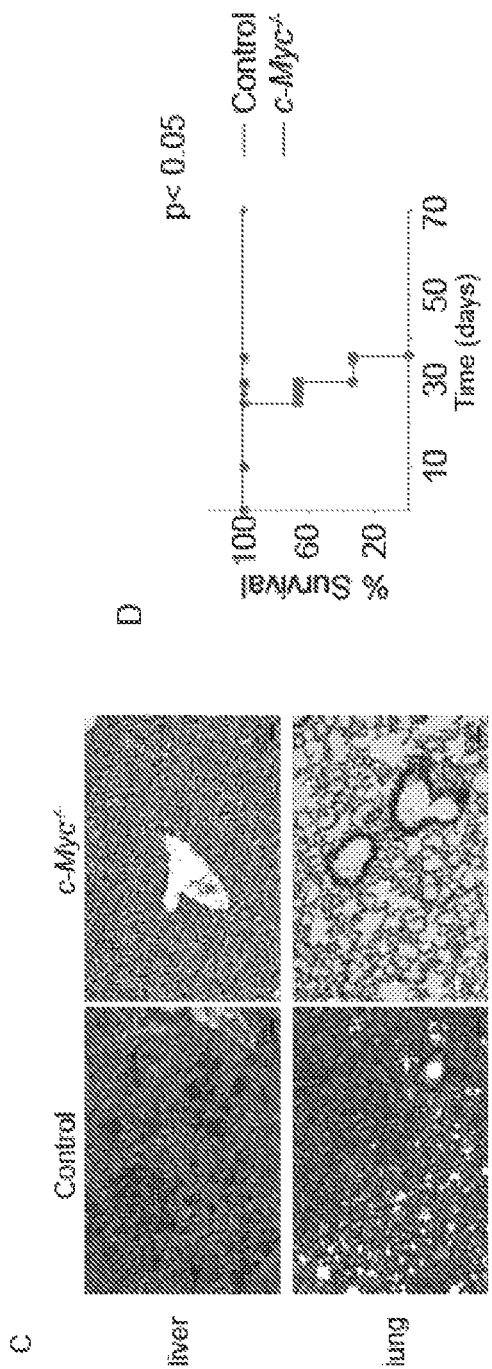

To test the importance of c-Myc protein expression in CML initiation and progression a conditional c-Myc allele (Mx1cre⁺c-Myc^(f/f)) was utilized. Flow-purified LSK cells from these animals (and littermate controls) were infected with Bcr-Abl-expressing retroviruses and transduced LSK cells were transplanted into irradiated hosts in an identical fashion to experiments previously described. Both genotypes prior to deletion were able to initiate disease as verified by peripheral blood analysis (FIG. 9B). Once disease onset was verified, c-Myc was deleted using polyI-polyC administration. Three weeks post deletion mice were analyzed for signs of disease progression. Deletion of c-Myc led to an almost complete absence of Bcr-Abl⁺ cells from the blood and secondary tissues such as liver and lung (FIGS. 9B and 9C). Mice carrying c-Myc⁻/⁻ Bcr-Abl⁺ cells were followed up to 6-8 months post cell transplantation and never developed any signs of a CML-like disease. On the other hand, control mice carrying Mx1cre⁺c-Myc⁺/⁺Bcr-Abl⁺ cells succumbed to a lethal CML-like disease within five weeks post transplantation (FIG. 9D).

Figures 11A, 11B, 11C:
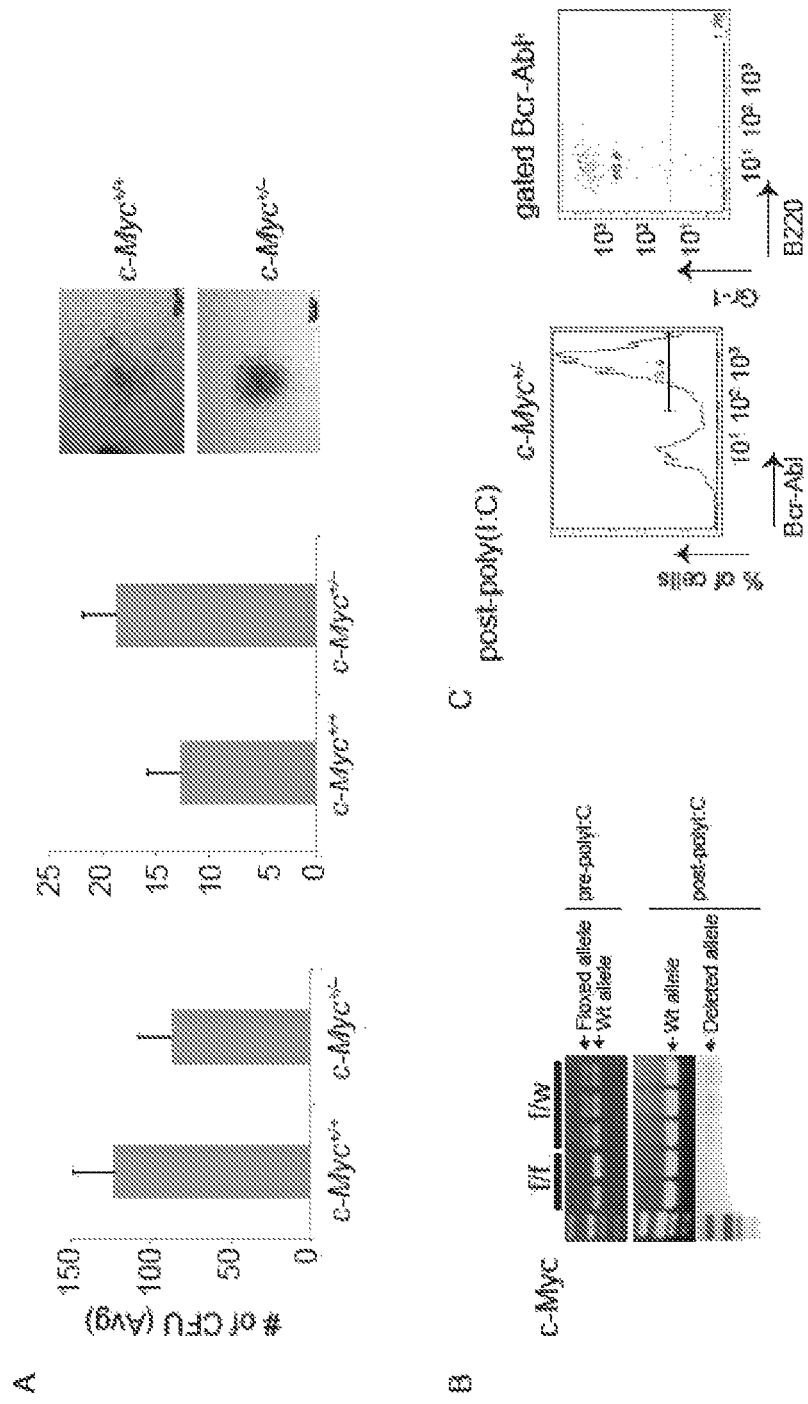
FIGS. 11A-11E demonstrate that the loss of one allele of c-Myc does not alter CML progression.
Figures 11D, 11E:
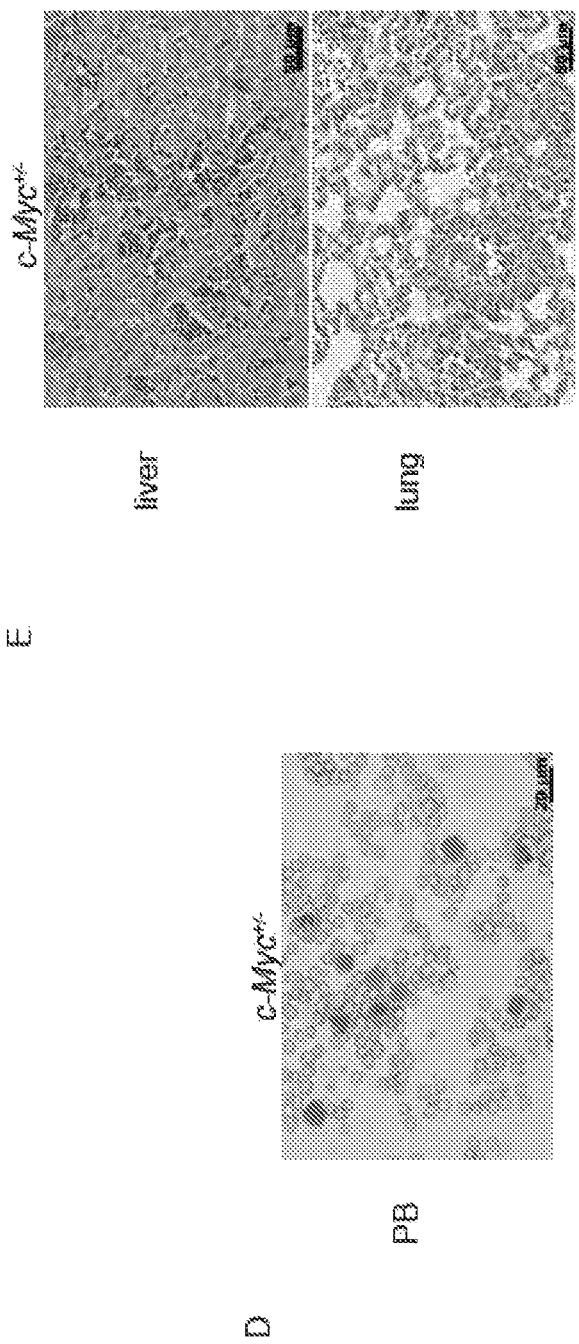

These studies indicate that there are well-defined thresholds of c-Myc protein expression, controlled by Fbw7-mediated ubiquitination, essential for CML induction and progression. Indeed, both lack of c-Myc expression and non-physiologically increased levels (in Mx1cre⁺Fbw7^(f/f) mice) are severely affecting CML progression. To further quantify c-Myc protein levels, Bcr-Abl-expressing LSK from mice carrying only one allele of c-Myc (Mx1cre⁺c-Myc^(f/w)) were utilized. These LSK cells express lower levels of c-Myc protein (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety). Initially, Bcr-Abl⁺ c-Myc⁺/⁻ LSK cells were able to generate colonies in vitro, at similar efficiency to Bcr-Abl⁺c-Myc⁺/⁺ counterparts in both primary and secondary platings (FIG. 11A). Disease was then initiated by transplanting Bcr-Abl-expressing LSK (Bcr-Abl⁺c-Myc⁺/⁻) cells, and upon verification of CML initiation one c-Myc allele was deleted. Interestingly, a single allele of c-Myc was sufficient to maintain disease progression in recipients (FIG. 11), suggesting once more that there are defined thresholds of c-Myc protein abundance essential for the progression of the disease.

Example 9

Fbw7 Deletion Inhibits Progression of Established, Bcr-Abl-Induced B-ALL

Figures 12A, 12B, 12C, 12D:
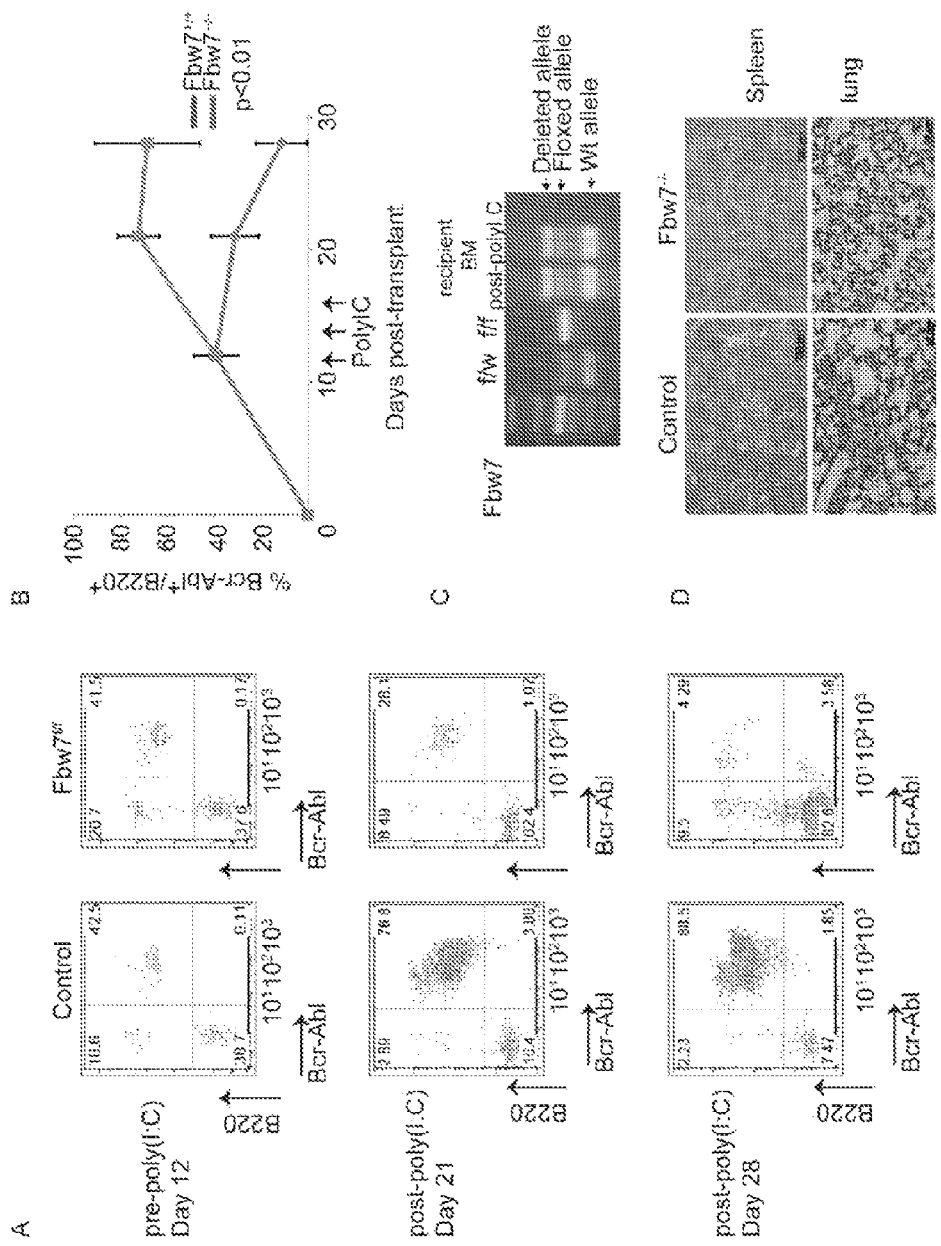
FIGS. 12A-12I show that depletion of Fbw7 inhibits progression of B-ALL.
Figures 12E, 12F, 12G, 12H, 12I:
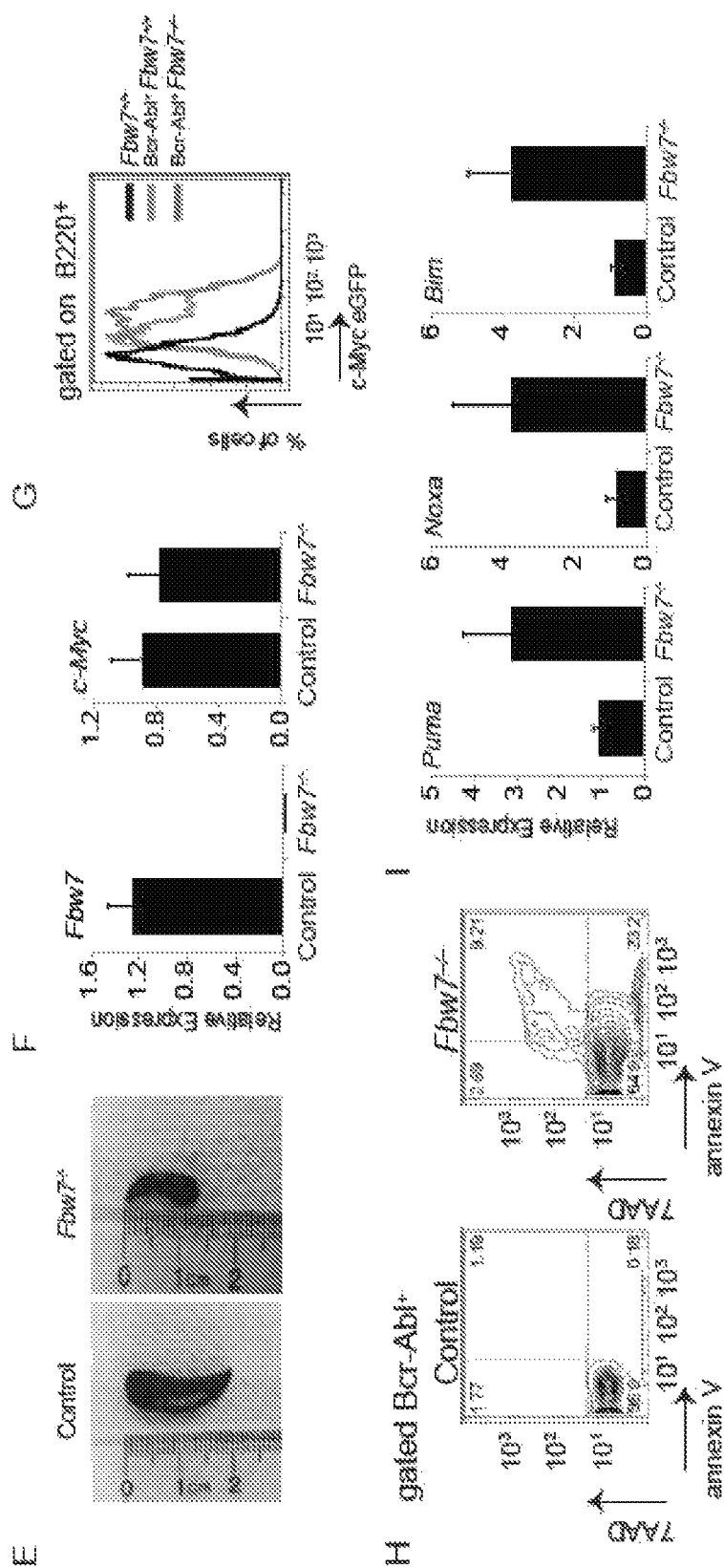

The Bcr-Abl translocation is also found in B-cell acute lymphoblastic leukemia (B-ALL). Whether Fbw7 plays a role in progression of B-ALL was determined. To establish B-ALL, MxCre⁺Fbw7^(w/w) or MxCre⁺Fbw7^(f/f) whole bone marrow was transduced with Bcr-Abl-GFP retrovirus followed by transplantation into lethally irradiated recipient mice. Peripheral blood was analyzed 12 days post transplantation to determine initiation of disease. Both cohorts of mice showed approximately 40% Bcr-Abl⁺ B220⁺ cells. At that point, deletion of Fbw7 was initiated by administration of polyI-polyC (FIG. 12A) and disease progression was monitored. As expected, mice transplanted with Bcr-Abl⁺ MxCre⁺ Fbw7^(w/w) BM had an increase in the percentage of Bcr-Abl⁺ B220⁺ cells in the peripheral blood. However, mice transplanted with Bcr-Abl⁺ MxCre⁺Fbw7^(f/f) BM showed a significant reduction in Bcr-Abl⁺ B220⁺ cells (FIG. 12A) and these cells were virtually undetectable three weeks after the initiation of Fbw7 deletion (FIG. 12B). MxCre⁺Fbw7⁺/⁺ mice showed signs of B-ALL including infiltration of secondary tissues and splenomegaly, whereas treated mice transplanted with MxCre⁺Fbw7^(f/f) showed no sign of B-ALL following deletion by polyI-polyC administration (FIGS. 12C-12E). Again utilizing the c-Myc^(eGFP) mouse model, c-Myc protein expression in the tumor was evaluated to determine whether loss of B-ALL was due to stabilization of c-Myc as previously seen in the CML model. Unlike the CML model ~100% of Bcr-Abl⁺ cells were B220⁺ and Bcr-Abl⁺ LSKs were not observed. Although a greater percentage of the tumor in Fbw7⁻/⁻ expressed c-Myc^(eGFP), there was no overall increase in expression suggesting Fbw7 has an alternative substrate in B-ALL (FIGS. 12F and 12G). Analysis of Annexin V and 7-AAD in the Bcr-Abl⁺ B220⁺ BM cells showed a significant increase in cell apoptosis and cell death along with induction of apoptosis associated p53 targets in MxCre⁺Fbw7⁻/⁻ BM (FIGS. 12H and 12I). This is an exciting finding as it suggests that Fbw7 could be an attractive therapeutic target also in Bcr-Abl⁺ B-ALL. In agreement with this notion, sequencing of FBW7 in human B-ALL patient cDNAs failed to identify any inactivating mutations (0/50 samples), suggesting that FBW7 function is required for B-ALL disease progression.

Example 10

Human CML Leukemia-Initiating Cells Require FBW7 Function

Figures 13A, 13B, 13C, 13D:
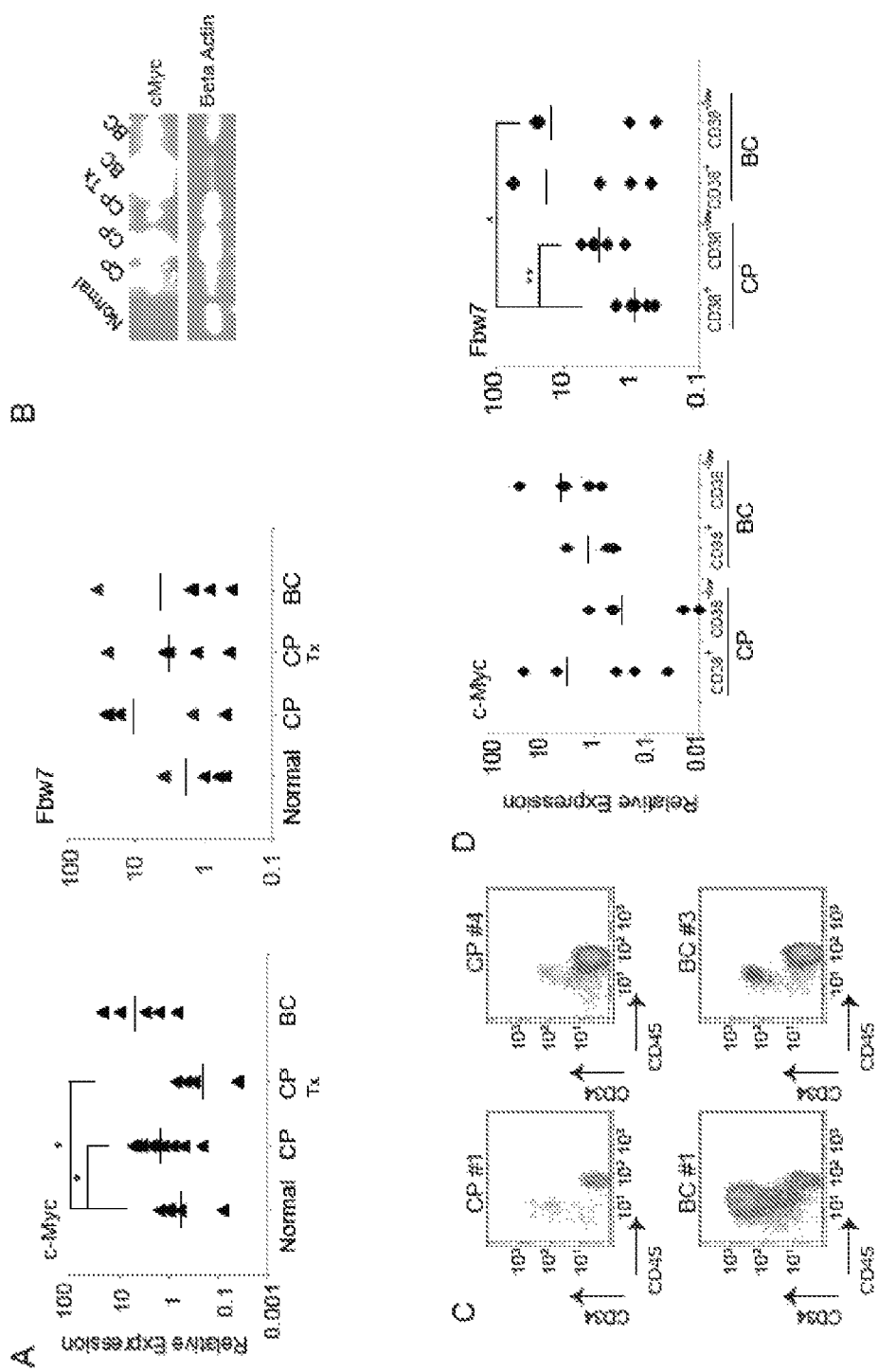
FIGS. 13A-13H demonstrate that human CML leukemia-initiating cells require FBW7 function.

Bcr-Abl induces c-Myc expression (Xie et al., "Jak2 is Involved in c-Myc Induction by Bcr-Abl," *Oncogene* 21:7137-7146 (2002), which is hereby incorporated by reference in its entirety). Consistent with these findings in peripheral blood mononuclear cells (PBMNCs), patients in chronic or blast phase expressed significantly higher levels of cMyc mRNA and protein than normal PBMNCs, where as, patients currently undergoing treatment with TKIs had significantly lower expression (FIGS. 13A and 13B). On the other hand, Fbw7 was detected in all normal and patient PBMNC, suggesting once more that Fbw7 function is not controlled at the level of mRNA transcription. The levels of c-Myc and Fbw7 expression in stem and progenitor populations in CML patients were determined by sorting CD34⁺CD38⁺ and CD34⁺CD38^(low) populations from four CP and BC patient BM samples (FIG. 13C). c-Myc expression was varied between patients and no significant differences were seen between in the stem and progenitor populations relative to expression in normal umbilical cord blood (UCB) (FIG. 13D). However, in chronic and blast phase patients Fbw7 was more highly expressed in stem cell enriched CD34⁺CD38^(low) population correlating to the expression previously observed in the mouse stem cell population (FIG. 13D).

Figures 13E, 13F, 13G, 13H:
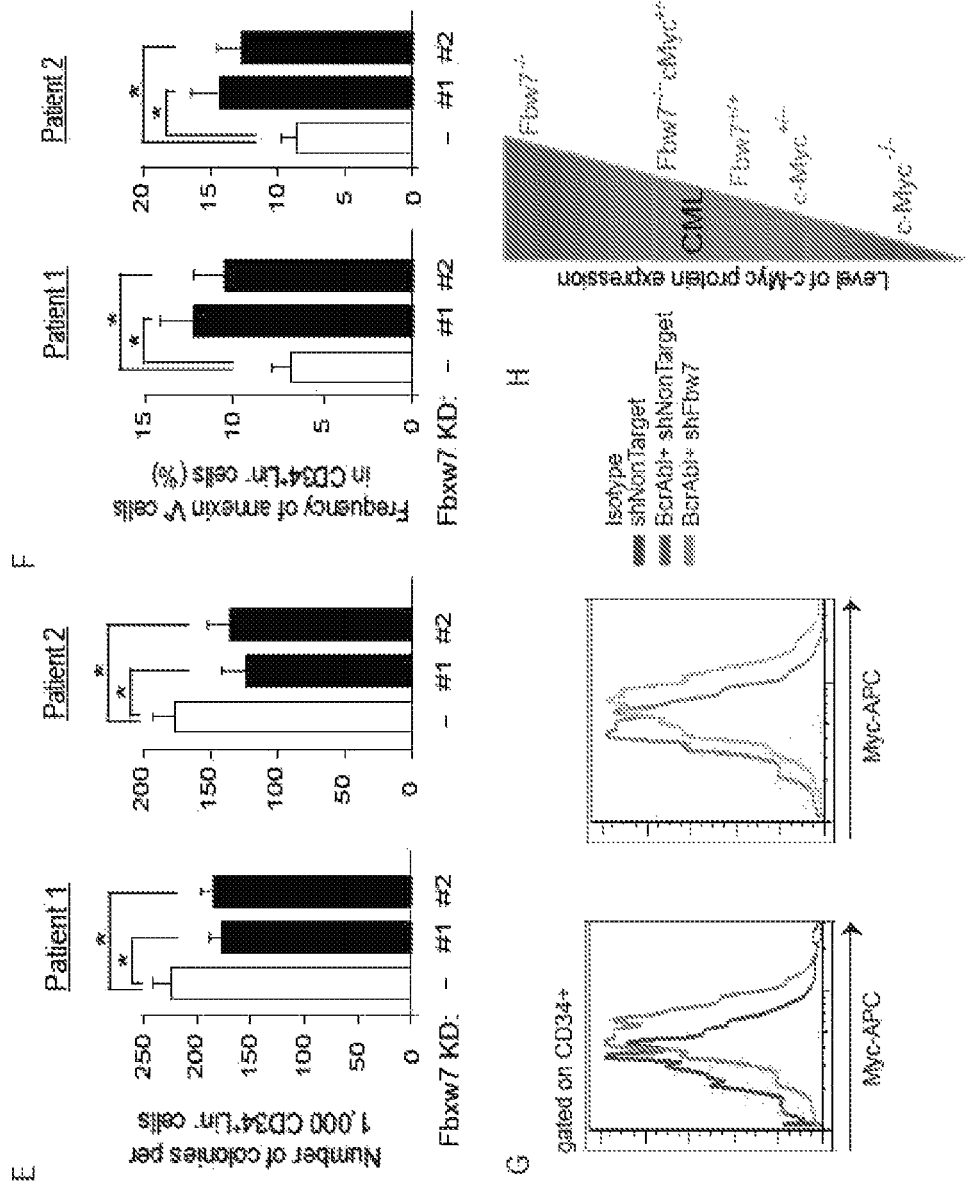
Figures 14A, 14B, 14C, 14D, 14E:
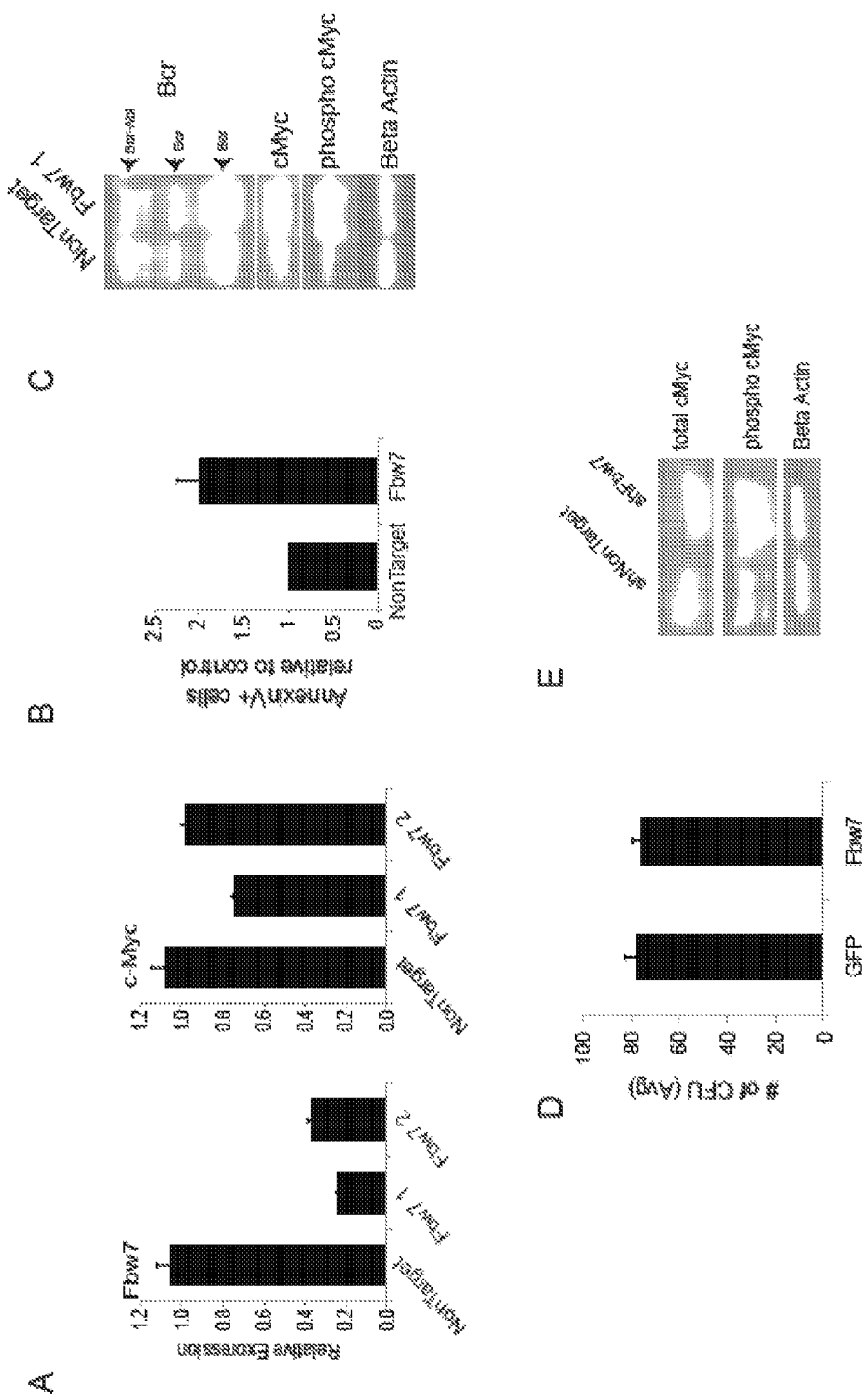
FIGS. 14A-14E depict the loss of Fbw7 in human CML cell line, KU812, and normal UCB derived CD34+.

To investigate the role of Fbw7 in human CML, Bcr-Abl⁺ CML cell line, KU812, was transduced with lentiviruses expressing shRNAs against Fbw7, and knockdown was confirmed with qRT-PCR (FIG. 14A). Knockdown of Fbw7 induced apoptosis and lead to the accumulation of c-Myc (FIGS. 14B and 14C). Moreover, degradation of c-Myc is preceded by phosphorylation by GSK3β, and Fbw7 silencing enriched specifically phosphorylated c-MYC. Fbw7 deletion in normal and patient derived CD34⁺ cells was tested. Silencing of Fbw7 did not alter colony forming ability of normal UCB derived CD34⁺ cells, but decreased self-renewal capacity of human CML-initiating cells (FIG. 13E and FIG. 14D). In agreement with the experiments performed using the mouse CML LSK cells, depletion of Fbw7 in human CD34⁺ cells significantly increased the frequency of cells undergoing cell death (FIG. 13F). Decrease of c-Myc activity using a small molecule inhibitor (10058-F4) rescued cells from apoptosis and their colony forming ability (Huang et al., "A Small-Molecule c-Myc Inhibitor, 10058-F4, Induces Cell-Cycle Arrest, Apoptosis, and Myeloid Differentiation of Human Acute Myeloid Leukemia," *Exp. Hematol.* 34:1480-1489 (2006), which is hereby incorporated by reference in its entirety). Also, consistent with mouse CML model, Bcr-Abl$^+$ CD34$^+$ cells expressed higher levels of c-Myc than normal CD34$^+$ cells, which was augmented following the loss of Fbw7 (FIG. 13G). Collectively, these results indicate that Fbw7 plays a pivotal role in the maintenance of human CML LICs by controlling c-Myc activity, suggesting once more that Fbw7 targeting is an attractive target for the treatment of CML.

Discussion of Examples 1-10

The essential function of the Fbw7 E3 ligase in the initiation and the progression of CML has been demonstrated herein using a well-established model of the disease and human primary CML. The interaction between Fbw7 and its substrate c-Myc controls the activity of CML leukemia-initiating cells. Fbw7 deletion leads to leukemia-initiating cell apoptosis due to high levels of c-Myc protein expression and activation of the p53 pathway. Genetic experiments showed that both down-regulation of c-Myc protein levels and inhibition of p53 activity can "rescue" LIC activity and disease progression. Interestingly, p53 mutations can accompany disease progression in human CML and p53 loss in some cases impedes the anti-leukemic response to BCR-ABL inhibition (Kelman et al., "Rearrangements in the p53 Gene in Philadelphia Chromosome Positive Chronic Myelogenous Leukemia," *Blood* 74:2318-2324 (1989); Wendel et al., "Loss of p53 Impedes the Antileukemic Response to BCR-ABL Inhibition," *Proc. Nat'l. Acad. Sci. U.S.A.* 103:7444-7449 (2006), which are hereby incorporated by reference in their entirety). This suggests that loss of p53 in some tumors could constitute an adaptive response to the increase in the levels of c-Myc during CML progression. Overall, the Examples described herein indicate that Fbw7 ligase function is absolutely essential for the maintenance of non-toxic levels of c-Myc protein within CML LIC cells. Interestingly, although Fbw7 is a ubiquitin ligase capable of targeting a large number of protein substrates (including Notch, Cyclin E, mTOR, MCL1 and c-jun), the biochemical and genetic rescue experiments suggest that c-Myc is the main protein substrate in CML, in contrast with T-ALL, where Notch1 appears to be one of the main ubiquitinated targets (O'Neil et al., "FBW7 Mutations in Leukemic Cells Mediate NOTCH Pathway Activation and Resistance to Gamma-Secretase Inhibitors," *J. Exp. Med.* 204:1813-1824 (2007); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety).

c-Myc protein abundance was visualized in vivo. c-Myc expression is restricted within the LIC population, with the bulk of the tumor being c-Myc$^{neg}$. These studies showed that Fbw7 function is specifically required by cells with leukemia-initiating activity but is dispensable for the maintenance of the more differentiated CML fraction. Moreover, genetic deletion of c-Myc during disease progression showed that Bcr-Abl-driven CML is addicted to physiological c-Myc function, suggesting that the disease requires well-defined and Fbw7-regulated thresholds of c-Myc abundance and activity (FIG. 13G). This is a novel and intriguing idea with potential important clinical ramifications in the field of cancer biology, as it indicates that both depletion and over-abundance of c-Myc protein levels in tumors leads to similar clinical outcomes, albeit with distinct mechanisms of action.

Recent development of small molecules targeting c-Myc co-activator bromodomain inhibitors (Delmore et al., "BET Bromodomain Inhibition as a Therapeutic Strategy to Target c-Myc," *Cell* 146:904-917 (2011), which is hereby incorporated by reference in its entirety) opens the way for therapeutic protocols that include c-Myc activity inhibition in established CML.

The notion that Bcr-Abl is able to induce c-Myc expression is not new, as classic experiments have shown that introduction of v-abl in a myeloid cell line can specifically induce c-Myc expression in a tyrosine kinase-dependent manner (Cleveland et al., "Tyrosine Kinase Oncogenes Abrogate Interleukin-3 Dependence of Murine Myeloid Cells Through Signaling Pathways Involving c-Myc: Conditional Regulation of c-Myc Transcription by Temperature-Sensitive V-Abl," *Mol. Cell. Biol.* 9:5685-5695 (1989), which is hereby incorporated by reference in its entirety). Subsequent seminal studies by Sawyers and colleagues demonstrated that Bcr-Abl-induced transformation could be suppressed by dominant negative MYC mutants in vitro (Sawyers et al., "Dominant Negative MYC Blocks Transformation by ABL Oncogenes," *Cell* 70:901-910 (1992), which is hereby incorporated by reference in its entirety). In agreement with these studies in vivo c-Myc protein levels in progressing CML were visualized and the populations that retain c-Myc protein expression were identified. Interestingly, only a minority (<20%) of the established leukemia is expressing c-Myc$^{eGFP}$. These cells are characterized by the expression of c-Kit and include the CML LSK population, previously suggested to include all LIC activity (Neering et al., "Leukemia Stem Cells in a Genetically Defined Murine Model of Blast-Crisis CML," *Blood* 110:2578-2585 (2007); Reynaud et al., "IL-6 Controls Leukemic Multipotent Progenitor Cell Fate and Contributes to Chronic Myelogenous Leukemia Development," *Cancer Cell* 20:661-673 (2011), which are hereby incorporated by reference in their entirety). When the c-Myc-expressing population was subdivided using the c-Myc$^{eGFP}$ reporter, disease was transplanted using only using the c-Myc$^{eGFP}$ LSK fraction suggesting that although LIC activity lies within the c-Myc-expressing fraction, c-Myc protein expression is not sufficient to guarantee leukemia-initiating properties. This is an intriguing distinction between normal and leukemic hematopoiesis as it has previously been shown that normal c-Myc$^{eGFP}$ LSK cells are multi-potential progenitors but not bona fide HSC (Reavie et al., "Regulation of Hematopoietic Stem Cell Differentiation by a Single Ubiquitin Ligase-Substrate Complex," *Nat. Immunol.* 11:207-215 (2010), which is hereby incorporated by reference in its entirety).

Fbw7 is required for normal hematopoiesis, as its deletion leads to progressive adult stem cell exhaustion. However, the response of normal and malignant stem and progenitor cells to the deletion of Fbw7 is vastly distinct. Putative LIC respond acutely, as Fbw7 deletion leads to rapid (<2 wks) loss of cell numbers and activity, as proven by secondary transplantation experiments. On the other hand, the response of physiological HSC is delayed and there are no significant changes in the number of HSC cells until 10-12 weeks post polyI-polyC-mediated Fbw7 gene deletion (Matsuoka et al., "Fbxw7 Acts as a Critical Fail-Safe Against Premature Loss of Hematopoietic Stem Cells and Development of T-ALL," *Genes Dev.* 22(8):986-91 (2008); Thompson et al., "Control of Hematopoietic Stem Cell Quiescence by the E3 Ubiquitin Ligase Fbw7," *J. Exp. Med.* 205:1395-1408 (2008), which are hereby incorporated by reference in their entirety). This differential response to Fbw7 deletion can be explained by the significantly higher levels of c-Myc protein in the Bcr-Ablexpressing LIC, as shown in vivo using the C-Myc$^{eGFP}$ knock-in model (FIGS. 6B-6D). This data indicates that it is possible to define a "therapeutic window" altering either the concentration of the inhibitor or the length of the treatment. Drug combination could be another therapeutic avenue, especially as tyrosine kinase inhibitors (TKI) fail to target CML-initiating cells. Indeed, Fbw7 inhibition can be used in combination with other established CML treatments, including Imatinib to achieve efficient targeting of CML-initiating cells.

Recent studies suggest that FBW7 small molecule targeting is a feasible approach. A biplanar dicarboxylic acid compound has recently been identified as an inhibitor of substrate recognition by the yeast Fbw7 ortholog (Cdc4) (Aghajan et al., "Chemical Genetics Screen for Enhancers of Rapamycin Identifies a Specific Inhibitor of an SCF Family E3 Ubiquitin Ligase," *Nat. Biotechnol.* 28:738-742 (2010); Orlicky et al., "An Allosteric Inhibitor of Substrate Recognition by the SCF (Cdc4) Ubiquitin Ligase," *Nat. Biotechnol.* 28:733-737 (2010), which are hereby incorporated by reference in their entirety). Moreover, as Fbw7-mediated c-Myc recognition is induced by the priming phosphorylation of c-Myc$^{Thr58}$ by GSK3, GSK3 inhibitors could also be used to target Fbw7 function and c-Myc stability. Such inhibitors have been developed and their efficacy in vivo was tested using MLL-induced models of AML (Wang et al., "Glycogen Synthase Kinase 3 in MLL Leukaemia Maintenance and Targeted Therapy," *Nature* 455:1205-1209 (2008), which is hereby incorporated by reference in its entirety). Moreover, such GSK3 inhibitors are currently in Phase II clinical trials for the treatment of Alzheimer's disease (Martinez et al., "Glycogen Synthase Kinase 3 Inhibitors in the Next Horizon for Alzheimer's Disease Treatment," *Int. J. Alzheimers Dis.* 2011:280502 (2011), which is hereby incorporated by reference in its entirety) opening the way for their future use for the treatment of CML in combination with Imatinib or latest generation tyrosine kinase inhibitors. Finally, as c-Myc activity is a driver of distinct tumor types, it is conceivable that Fbw7 inhibitors could be promising therapeutic tools in a wide range of blood and solid tumors.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting proliferation of leukemia cells said method comprising:
   administering to a population of leukemia cells a Fbw7 inhibitor, wherein the Fbw7 inhibitor is 1-(2-carboxynaphth-lyl)-2-naphthoic acid (SCF-12), in an amount.

2. The method of claim 1, wherein the population of leukemic cells are selected from the group consisting of chronic myeloid leukemia cells, acute myeloid leukemia cells, and B-cell acute lymphoblastic leukemia cells.

3. The method of claim 1, wherein the population of leukemia cells comprise a population of leukemic initiating cells.

4. The method of claim 3, wherein the population of leukemic initiating cells comprises a population of $BCR-ABL^+$ $CD34^+CD38^-$ cells.

5. The method of claim 1, wherein said administering is in vivo.

6. The method according to claim 1, wherein said administering is carried out in combination with another leukemia therapeutic.

7. The method according to claim 6, wherein the leukemia therapeutic comprises a tyrosine kinase inhibitor.

8. The method according to claim 7, wherein the tyrosine kinase inhibitor is selected from the group consisting of imatinib mesylate, nilotinib, and dasatinib.

9. The method according to claim 6, wherein the leukemia therapeutic is selected from the group consisting of a chemotherapeutic agent, radiation, an anti-angiogenic agent, an immune-enhancing agent, and combinations thereof.

10. The method according to claim 9, wherein the leukemia therapeutic is a chemotherapeutic agent selected from the group consisting of cytarabine, cyclophosphamide, vincristine, prednisone, daunorubicin, PEG asparaginase, methotrexate, and leucovorin.

* * * * *

UNITED STATES PATENT AND TRADEMARK OFFICE
CERTIFICATE OF CORRECTION

PATENT NO. : 9,241,920 B2
APPLICATION NO. : 14/354822
DATED : January 26, 2016
INVENTOR(S) : Aifantis et al.

Page 1 of 1

It is certified that error appears in the above-identified patent and that said Letters Patent is hereby corrected as shown below:

In the claims

In claim 1, at col. 45, line 43, after the word "amount", please insert --effective to inhibit leukemia cell proliferation--

In claim 1, at col. 45, line 43, delete "SCF-12" and insert --SCF-I2--

Signed and Sealed this
Seventh Day of June, 2016

Michelle K. Lee
*Director of the United States Patent and Trademark Office*